United States Patent [19]

Rody et al.

[11] Patent Number: 5,032,498

[45] Date of Patent: Jul. 16, 1991

[54] COMPOSITIONS AND PHOTOGRAPHIC MATERIALS CONTAINING 2-(2-HYDROXYPHENYL)-BENZTRIAZOLES, AS UV-ABSORBERS

[75] Inventors: Jean Rody, Riehen; Mario Slongo, Muttenz, both of Switzerland

[73] Assignee: Ciba-Geigy Corporation, Ardsley, N.Y.

[21] Appl. No.: 570,474

[22] Filed: Aug. 21, 1990

Related U.S. Application Data

[60] Division of Ser. No. 310,178, Feb. 13, 1989, Pat. No. 4,973,702, which is a division of Ser. No. 122,554, Nov. 12, 1987, Pat. No. 4,853,471, which is a continuation of Ser. No. 869,819, May 30, 1986, abandoned, which is a continuation of Ser. No. 608,529, May 9, 1984, abandoned, which is a continuation of Ser. No. 339,254, Jan. 13, 1982, abandoned.

[30] Foreign Application Priority Data

Jan. 23, 1981 [CH] Switzerland ............... 437/81

[51] Int. Cl.$^5$ ............................ G03C 1/815
[52] U.S. Cl. ..................... 430/512; 430/931; 524/91; 526/259; 544/132; 544/368; 546/226; 548/261; 548/259; 548/260
[58] Field of Search ............... 430/519, 931; 524/91; 526/259; 544/132, 368; 546/226; 548/261, 259, 260

[56] References Cited

U.S. PATENT DOCUMENTS

| | | | |
|---|---|---|---|
| 3,214,436 | 10/1965 | Boyle et al. | 548/260 |
| 3,230,194 | 1/1966 | Boyle | 548/260 |
| 3,399,173 | 8/1968 | Heller et al. | 548/261 |
| 3,629,191 | 12/1971 | Heller et al. | 548/261 |
| 4,256,881 | 3/1981 | Simons et al. | 544/132 |
| 4,289,686 | 9/1981 | Rody et al. | 546/226 |
| 4,347,180 | 8/1982 | Winter et al. | 260/206 |
| 4,716,234 | 12/1987 | Dunks | 548/260 |
| 4,785,063 | 11/1988 | Slongo et al. | 548/261 |
| 4,791,206 | 12/1988 | O'Neil | 544/132 |
| 4,853,471 | 8/1989 | Rody et al. | 548/261 |

FOREIGN PATENT DOCUMENTS

| | | | |
|---|---|---|---|
| 269087 | 6/1962 | Australia | 548/261 |
| 0010516 | 4/1980 | European Pat. Off. | |
| 3141622 | 9/1978 | Japan | 548/261 |
| 1212466 | 11/1970 | United Kingdom | 548/260 |

OTHER PUBLICATIONS

Chem. Abstr. vol. 93, Entry 169113 v (1980), Abstract Ciba Geigy JP 80/49355.
Papillo et al., "Stabilization of Polypropylene . . . ," Chem. Abst. 76:25997n (1972).
Karvas et al., "Light Stabilizers . . . " Chem. Abst. 70:48169, (1969).
Cho et al., "4-Chloro-2-(2'-Hydroxy-3',5'-Di-tertiary-Butyl-Phenyl) Benzotriazole", Chem. Abst. 89: 109505g, (1978).
Hariki et al., "Film for Cultivation of Beams," Chem. Abst. 93: 27450(d) (1980).
Maeda et al., "Films for Use in Agriculture," Chem. Abst. 89:7105j (1978).
Showa, "2-(2'-Hydroxy-3'-Tert. Butyl-5'-Methylphenyl)-5-Chlorobenzotriazole," Chem. Abst 96:52313f (1980).

Primary Examiner—Jack P. Brammer
Attorney, Agent, or Firm—Harry Falber

[57] ABSTRACT

The novel UV-absorbers are compounds of the formula

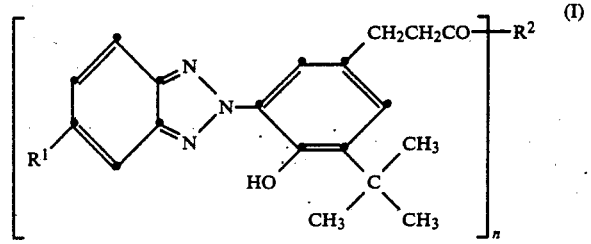

in which $R^1$ is, for example, hydrogen, n is one of the numbers 1 or 2 and $R^2$ is an appropriate monovalent or divalent radical, for example —OH or —O—CH$_2$CH$_2$—O—. The UV-absorbers are used in particular for stabilising and improving lacquers and photographic material.

10 Claims, No Drawings

COMPOSITIONS AND PHOTOGRAPHIC MATERIALS CONTAINING 2-(2-HYDROXYPHENYL)-BENZTRIAZOLES, AS UV-ABSORBERS

This is a divisional of application Ser. No. 310,178 now U.S. Pat. No. 3,497,702 filed on Feb. 13, 1989, which is a divisional of Ser. No. 122,554, filed on Nov. 12, 1987, now U.S. Pat. No. 4,853,471, which in turn was a continuation of application Ser. No. 869,819, filed May 30, 1986, now abandoned, which in turn was a continuation of application Ser. No. 608,529, filed May 9, 1984, now abandoned, which in turn was a continuation of application Ser. No. 339,254, filed Jan. 13, 1982, now abandoned.

The invention relates to novel 2-(2-hydroxyphenyl)-benztriazoles which are used as UV-stabilisers for organic material, in particular in plastics and in photographic material.

Light stabilisers for plastics which are based on benztriazoles and which contain on the aromatic substituent in the 2-position of the benztriazole nucleus only one OH group and a branched alkyl group, but otherwise no functional groups, are already known. Examples of such UV-absorbers are 2-(2-hydroxy-3,5-dicumylphenyl)-benztriazole and 2-(2-hydroxy-5-tert.-butylphenyl)-benztriazole. Some of these known UV-stabilisers can only be prepared by expensive processes.

In addition, they are for the most part sparingly soluble and relatively volatile. They have a strong tendency to crystallise and migrate. These properties, which are very unfavourable for UV-stabilisation, cause considerable problems when the products are used in plastics and/or lacquers, such as automobile lacquers.

U.S. Pat. No. 3,766,205 describes light stabilisers of the formula

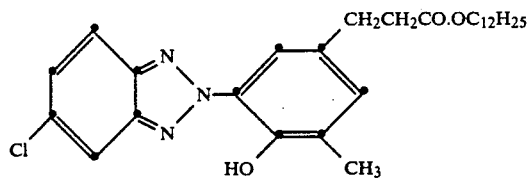

which are employed, for example, in polyamides and polyesters. They exhibit the same disadvantages as the UV-stabilisers described above. Japanese Patent Application Sho No. 54-95,233 describes similar light stabilisers, for example of the formula

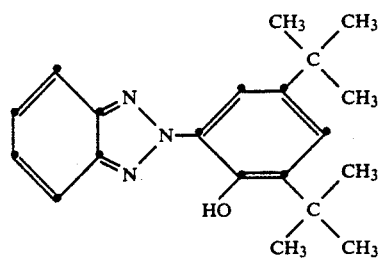

which are employed together with co-stabilisers in materials for colour photography. Like the light stabilisers described above, these stabilisers do not have an optimal action.

Protection against damage caused by UV light is particularly important in photographic technology and especially in colour photographic technology.

In order to protect the components (in particular dyes and couplers) present in a colour photographic material as effectively as possible against destruction by ultraviolet light, UV absorbers are normally inserted into one or more of the upper layers of the material. This is effected as a rule by dissolving the UV-absorber in a high-boiling solvent and dispersing this solution, in the form of very fine droplets, in the appropriate coating solution. Since these droplets have a disadvantageous effect on the mechanical properties of the layer, and can "exude" if they are in the top layer of the material, it is important to keep the quantity of absorber solution as small as possible. This also makes it possible to produce thinner layers, which, in turn, offers advantages in processing (carry-over between baths and drying). It is therefore desirable to employ UV-absorbers which have as high a solubility as possible in the customary high-boiling solvents. The UV-absorbers of the state of the art, for example the stabilisers disclosed in Japanese Application Sho No. 54-95,233 do not, to a satisfactory extent, fulfil this requirement either.

It has now been found that the products of the present invention have an extremely high solubility in the high-boiling solvents and are therefore superior to the products of the state of the art in the photographic field too. In some cases they are actually liquid and can be employed in a colour photographic material without highboiling solvents. Moreover, they are also sparingly volatile and do not tend to crystallise.

The invention relates to compounds of the formula I

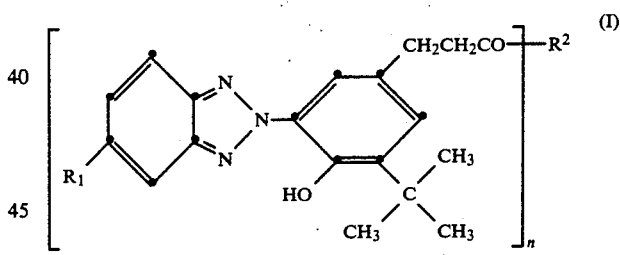

in which $R^1$ is H, Cl, straight-chain or branched $C_1$–$C_4$ alkyl or straight-chain or branched $C_1$–$C_4$ alkoxy and n is one of the numbers 1 or 2, and in which, a) in the event that n=1, $R^2$ is Cl, —$OR^3$ or

and b) in the event that n=2, $R^2$ is one of the divalent radicals —O—$R^9$—O— or

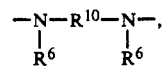

$R^3$ being H, straight-chain or branched $C_1$–$C_{18}$ alkyl which is unsubstituted or substituted by 1 to 3 OH groups or

or —O—Si(R⁶)₃ or —O—CO(R⁶), straight-chain or branched $C_3$-$C_{18}$ alkyl which is interrupted by —O—, —S— or —NR⁶— and which can be unsubstituted or substituted by OH or —O—CO(R⁶), $C_5$-$C_{12}$ cycloalkyl which is unsubstituted or substituted by OH, straight-chain or branched $C_2$-$C_{18}$ alkenyl which is unsubstituted or substituted by OH, $C_7$-$C_{15}$ aralkyl,

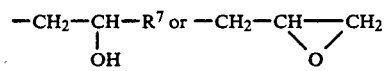

and $R^4$ and $R^5$ independently of one another being H, straight-chain or branched $C_1$-$C_{18}$ alkyl, straight-chain or branched $C_3$-$C_{18}$ alkyl which is interrupted by O, S or —NR⁶—, $C_5$-$C_{12}$ cycloalkyl, $C_6$-$C_{14}$ aryl which is substituted or unsubstituted, straight-chain or branched $C_3$-$C_8$ alkenyl, $C_7$-$C_{15}$ aralkyl, $C_6$-$C_{14}$ aryl or $C_1$-$C_3$ hydroxyalkyl, or $R_4$ and $R_5$, together with the nitrogen atom, are a pyrrolidine, piperidine, piperazine or morpholine ring, and $R_6$ being H, straight-chain or branched $C_1$-$C_{18}$ alkyl, $C_5$-$C_{12}$ cycloalkyl, straight-chain or branched $C_3$-$C_8$ alkenyl, $C_6$-$C_{14}$ aryl or $C_7$-$C_{18}$ aralkyl, $R_7$ being H, straight-chain or branched $C_1$-$C_{18}$ alkyl which is unsubstituted or substituted by —PO(OR⁸)₂, phenyl which is unsubstituted or substituted by OH, $C_7$-$C_{18}$ aralkyl or —CH₂OR⁸, $R^8$ being straight-chain or branched $C_1$-$C_{18}$ alkyl, straight-chain or branched $C_3$-$C_{18}$ alkenyl, $C_5$-$C_{10}$ cycloalkyl, $C_6$-$C_{16}$ aryl or $C_7$-$C_{15}$ aralkyl, $R^9$ being $C_2$-$C_8$ alkylene, $C_4$-$C_8$ alkenylene, $C_4$ alkinylene, cyclohexylene, straight-chain or branched $C_4$-$C_{10}$ alkylene which is interrupted by —O—, or

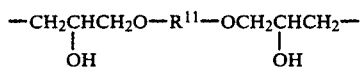

and $R_{10}$ being straight-chain or branched $C_2$-$C_{12}$ alkylene which may be interrupted by —O—, cyclohexylene,

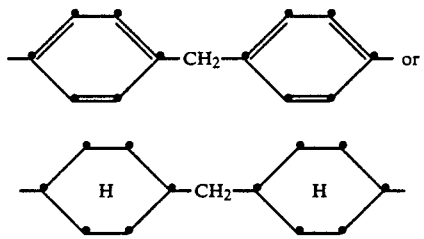

or $R^{10}$ and $R^6$, together with the two nitrogen atoms, being a piperazine ring, and $R^{11}$ being straight-chain or branched $C_2$-$C_8$ alkylene, straight-chain or branched $C_4$-$C_{10}$ alkylene which is interrupted by —O—, cycloalkylene, arylene,

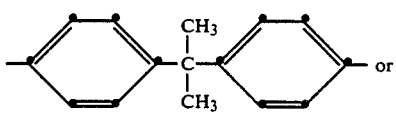

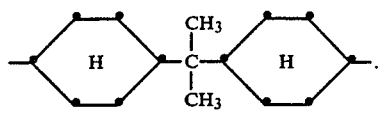

As an alkyl radical, $R^1$ can be methyl, ethyl, propyl, i-propyl, butyl and tert.-butyl, while as an alkoxy radical it can be methoxy, ethoxy, propoxy and butoxy.

$R^3$, $R^4$, $R^5$, $R^6$, $R^7$ and $R^8$ can be the following alkyl radicals, for example: methyl, isopropyl, n-butyl, sec.-butyl, tert.-butyl, tert.-amyl, 2-ethylhexyl, n-octyl, 1,1,3,3-tetramethylbutyl, n-dodecyl, 1,1,7,7-tetramethyloctyl and n-octadecyl.

$R^3$, $R^4$ and $R^5$ can be the following $C_3$-$C_{18}$ alkyl radicals which are interrupted by O, S or —NR⁶— and can be substituted by OH: methoxyethyl, ethoxyethyl, butoxyethyl, butoxypropyl, methylthiaethyl, CH₃OCH₂CH₂OCH₂CH₂—, CH₃CH₂OCH₂CH₂OCH₂CH₂—, C₄H₉OCH₂CH₂OCH₂CH₂—, ethylthiapropyl, octylthiapropyl, dodecyloxypropyl, 2-hydroxyethyl, 2-hydroxypropyl, 4-hydroxybutyl, 6-hydroxyhexyl, —CH₂CH₂—NH—C₄H₉, —CH₂CH₂CH₂NH—C₈H₁₇ and

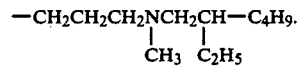

$R^3$, $R^4$, $R^5$, $R^6$ and $R^8$ can be the following $C_5$-$C_{12}$ cycloalkyl radicals: cyclopentyl, cyclohexyl, cycloheptyl, cyclooctyl or cyclodecyl. In the case of $R^3$, the radical can also be substituted by OH.

$R^4$, $R^5$ and $R^6$ can be the following alkenyl radicals: allyl, methallyl, 2-n-hexenyl or 4-n-octenyl.

If $R^3$ is alkenyl, it can have the same meaning as $R^4$, $R^5$ and $R^6$ as alkenyl radicals, but it can also be —CH=CH₂, 10-n-undecenyl or 9-n-octadecenyl, and it is also possible for the radical $R^3$ to be substituted by OH.

$R^4$ and $R^5$ can be the following $C_7$-$C_{15}$ aralkyl radicals: benzyl, α-phenylethyl, 2-phenylethyl or 4-tert.-butylbenzyl.

If $R^3$, $R^6$, $R^7$ or $R^8$ are aralkyl, they can, independently of one another, have the same meaning as $R^4$ or $R^5$.

Independently of one another, $R^4$, $R^5$ and $R^6$ can be the following $C_6$-$C_{14}$ aryl radicals: phenyl, α-naphthyl or β-naphthyl.

If $R^4$ and $R^5$ are $C_1$-$C_3$ hydroxyalkyl, this can be the following radicals: hydroxymethyl, hydroxyethyl or hydroxypropyl.

As $C_2$-$C_8$ alkylene, $R^9$ and $R^{11}$ can be the following radicals: ethylene, propylene, butylene, hexylene or octylene.

As alkylene, $R^{10}$ can be the same radicals, but can, in addition, also be higher-molecular groups, such as decylene or dodecylene.

If $R^9$ is a $C_4$-$C_8$ alkenylene radical, the following is an example of a suitable group: butenylene.

In the case of $R^9$ and $R^{11}$, suitable straight-chain or branched $C_4$-$C_{10}$ alkylene groups which are interrupted by O are the following groups: —CH₂CH₂OCH₂CH₂—,

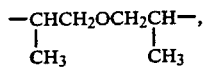

—CH$_2$CH$_2$OCH$_2$CH$_2$OCH$_2$CH$_2$— and —CH$_2$C-H$_2$OCH$_2$CH$_2$OCH$_2$CH$_2$OCH$_2$CH$_2$—.

If R$^{11}$ is a cycloalkylene radical, the following groups are embraced: 1,3-cyclohexylene and 1,4-cyclohexylene.

If R$^{11}$ is arylene, this can be, specifically, the following groups: 1,3-phenylene or 1,4-phenylene.

A preferred form of the invention is constituted by compounds of the formula I in which R$^1$ is H or Cl, n is the number 1 and R$^2$ is —OR$^3$ or

R$^3$ being straight-chain or branched C$_4$–C$_{12}$ alkyl, straight-chain or branched C$_3$–C$_{10}$ alkyl which is interrupted by O, cyclohexyl or

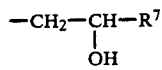

which is unsubstituted or substituted by OH, R$^4$ and R$^5$ independently of one another being straight-chain or branched C$_4$–C$_{12}$ alkyl, straight-chain or branched C$_3$–C$_{10}$ alkyl which is interrupted by O, or cyclohexyl, R$^7$ being straight-chain or branched C$_1$–C$_{12}$ alkyl which is unsubstituted or substituted by

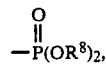

or —CH$_2$OR$^8$, and R$^8$ being straight-chain or branched C$_1$–C$_{12}$ alkyl or cyclohexyl.

A further preferred form of the invention is constituted by compounds of the formula I in which R$^1$ is H or Cl, n is the number 2 and R$^2$ is one of the divalent radicals —O—R$^9$—O— or

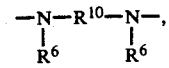

R$^6$ being H or C$_1$–C$_8$ alkyl, R$^9$ being C$_2$–C$_6$ alkylene, straight-chain or branched C$_4$–C$_{10}$ alkylene which is interrupted by —O—, or

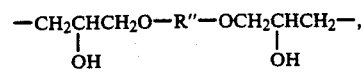

R$^{10}$ being straight-chain or branched C$_2$–C$_{12}$ alkylene and R$^{11}$ being C$_2$–C$_6$ alkylene or straight-chain or branched C$_4$–C$_{10}$ alkylene which is interrupted by O.

The following are typical representatives of compounds of the formula I in which n is the number 1: 2-[2-hydroxy-3-tert.-butyl-5-(2-carboxyethyl)-phenyl]-benztriazole, 2-[2-hydroxy-3-tert.-butyl-5-(2-carboxyethyl)-phenyl]-5-chlorobenztriazole, 2-[2-hydroxy-3-tert.-butyl-5-(2-chlorocarbonylethyl)-phenyl]-benztriazole, 2-[2-hydroxy-3-tert.-butyl-5-(2-chlorocarbonylethyl)-phenyl]-5-chlorobenztriazole, 2-[2-hydroxy-3-tert.-butyl-5-(2-carbomethoxyethyl)-phenyl]-benztriazole, 2-[2-hydroxy-3-tert.-butyl-5-(2-carbomethoxyethyl)-phenyl]-5-chlorobenztriazole, 2-[2-hydroxy-3-tert.-butyl-5-(2-carbocyclohexyloxyethyl)-phenyl]-benztriazole, 2-[2-hydroxy-3-tert.-butyl-5-(2-carbooctyloxyethyl)-phenyl]-benztriazole, 2-{2-hydroxy-3-tert.-butyl-5-[2-carbo-(2-ethylhexyloxy)-ethyl]-phenyl}-benztriazole, 2-[2-hydroxy-3-tert.-butyl-5-(2-carboisodecyloxyethyl)-phenyl]-benztriazole, 2-[2-hydroxy-3-tert.-butyl-5-(2-carbododecyloxyethyl)-phenyl]-benztriazole, 2-[2-hydroxy-3-tert.-butyl-5-(2-carbododecyloxyethyl)-phenyl]-5-chlorobenztriazole, 2-[2-hydroxy-3-tert.-butyl-5-(2-carbooctyloxyethyl)-phenyl]-5-chlorobenztriazole, 2-{2-hydroxy-3-tert.-butyl-5-[2-carbo-(2-ethylhexyloxy)-ethyl]-phenyl}-5-chlorobenztriazole, 2-{2-hydroxy-3-tert.-butyl-5-[2-carbo-(2-hydroxycyclohexyloxy)-ethyl]-phenyl}-benztriazole, 2-[2-hydroxy-3-tert.-butyl-5-(2-carbopiperidylamidoethyl)-phenyl]-benztriazole, 2-[2-hydroxy-3-tert.-butyl-5-(2-carbomorpholinoamidoethyl)-phenyl]-benztriazole and 2-{2-hydroxyl-3-tert.-butyl-5-[2-carbo-(3,5-di-tert.-butyl-4-hydroxyanilido)-ethyl]-phenyl}-benztriazole.

The following are typical representatives of compounds of the formula I in which n is the number 2:

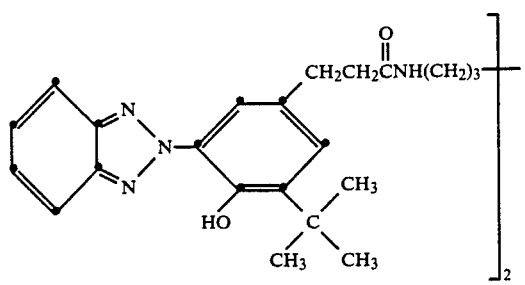

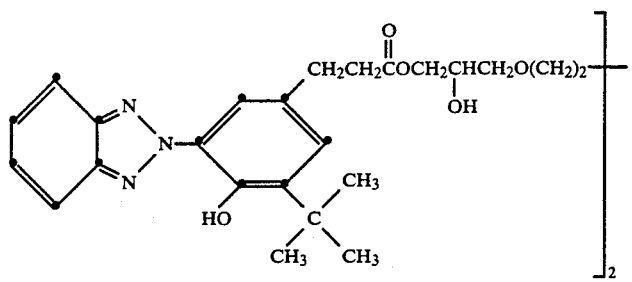

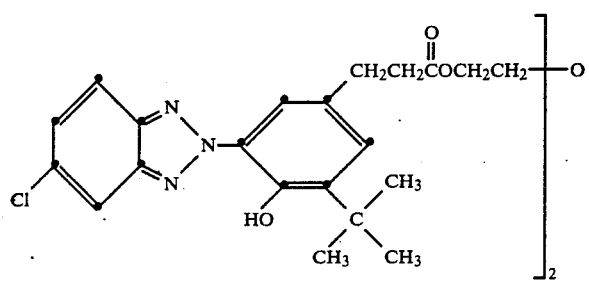

The following compounds are further preferred forms of the invention: 2-[2-hydroxy-3-tert.-butyl-5-(2-carbo-n-octyloxyethyl)-phenyl]-benztriazole, 2-{2-hydroxy-3-tert.-butyl-5-[2-carbo-(2-ethylhexyl)-oxyethyl]-phenyl}-benztriazole, 2-[2-hydroxy-3-tert.-butyl-5-(2-carbo-n-octyloxyethyl)-phenyl]-5-chlorobenztriazole, 2-{2-hydroxy-3-tert.-butyl-5-[2-carbo-(2-ethylhexyl)-oxyethyl]-phenyl}-5-chlorobenztriazole and the compound of the formula

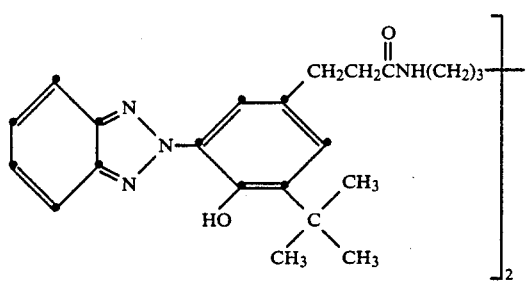

A further preferred form of the invention is also constituted by a mixture of compounds of the formula I in which 2-[2-hydroxy-3-tert.-butyl-5-(2-carbo-n-octyloxyethyl)-phenyl]-5-chlorobenztriazole and 2-{2-hydroxy-3-tert.-butyl-5-[2-carbo-(2-ethylhexyl)-oxyethyl]-phenyl}-5-chlorobenztriazole are present in a ratio by weight of 1:1.

The following procedure is used in the preparation, which is known per se, of the compounds, according to the invention, of the formula I. A substituted or unsubstituted o-nitroaniline is diazotised and the product is coupled with 2-(3-tert.-butyl-4-hydroxyphenyl)-propionic acid at pH 8 to pH 11. The dye is isolated after acidification. The reaction proceeds in accordance with the following equation

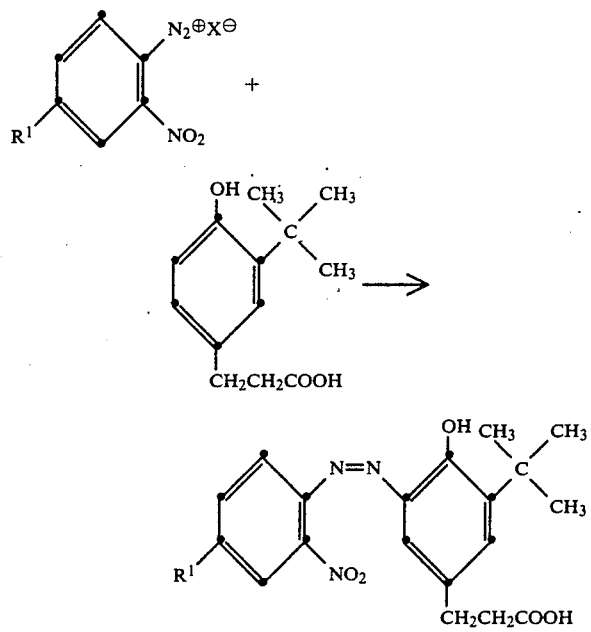

($X^\ominus$ is, for example, a halogen anion (such as $Cl^\ominus$), $-HSO_4^\ominus$ or $(BF_4)^\ominus$).

The corresponding benztriazolecarboxylic acid, which is itself a substance according to the invention, but which can also be used as a starting substance for other compounds of the formula I, is prepared from the resulting dye by reductive triazolisation under alkaline conditions. In the triazolisation under reducing conditions the reduction is preferably carried out catalytically by means of hydrogen, or zinc dust is used as the reducing agent. The reaction proceeds in accordance with the following equation:

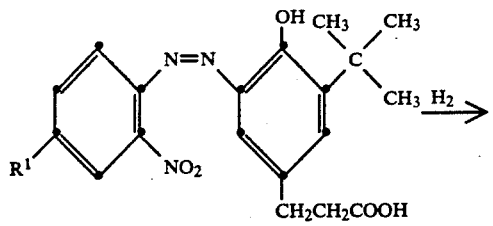

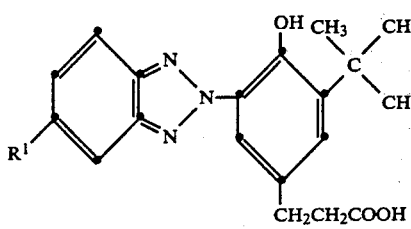

If the benztriazolecarboxylic acids which can be obtained in accordance with the above process are used further as starting materials for the preparation of other compounds embraced by the invention, the following procedures are used for the process of preparation:

1) If n is 1, direct esterification of these carboxylic acids with alcohols of the formula $R^{3'}OH$ ($R^{3'}$ has the same definition as the radical $R^3$ indicated previously, but is not

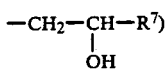

under a water separator in the presence of an acid catalyst; if n is 2, corresponding direct esterification with dialcohols of the formula $HO-R^9-OH$.

2) Reaction of the benztriazolecarboxylic acid with an epoxide in accordance with the following equation

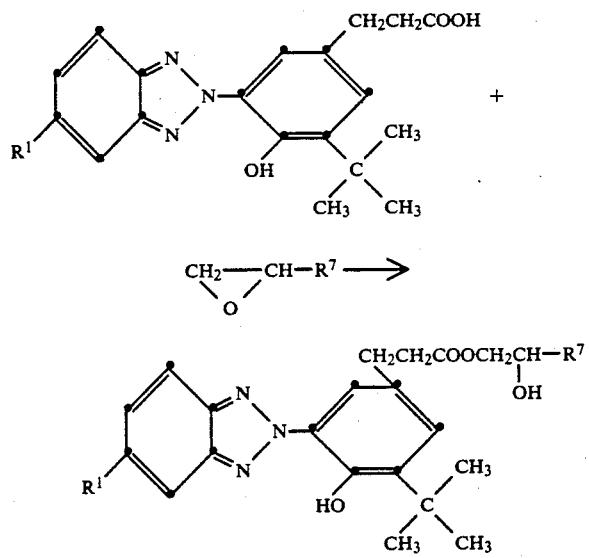

A further incorporation into lacquer binders is possible. This incorporation is possible in the preparation of the resin as well as in the chemical cross-linking of lacquer resins during the stoving process.

In the synthesis of the resin, the incorporation is effected, for example, by polycondensation (polyester resins or alkyd resins) or by polymerisation (acrylic resins), if $R^7$ contains a vinyl group. In the stoving process, the incorporation is effected by reacting the alcohol group with crosslinking agents, for example amino/formaldehyde resins or polyisocyanates.

3) Chlorination of the benztriazolecarboxylic acid by known processes to give the acid chloride, according to the invention, of the formula I. The starting acid is suspended in, for example, hexane, and thionyl chloride (a 50% excess) is added dropwise at room temperature. HCl and $SO_2$ are evolved in the form of gas in an exothermic reaction, and a solution is formed. The resulting acid chloride is stirred to complete the reaction at 60° C.

The benztriazole alkyl esters according to the invention which can be obtained by reaction 1 (in particular those having low-molecular alkyl groups, such as $-CH_3$ and $-C_2H_5$) and which can also be prepared, in addition, by other known processes for preparing esters, can also be employed as starting substances for the preparation of further compounds, according to the invention, of the formula I. For example, they are used in the following processes:

4) If n is 1 in formula I, transesterification of the benztriazolecarboxylic acid methyl ester according to the invention with alcohols of the formula $R^{3'}OH$ in the presence of a transesterification catalyst, such as tetrabutyl orthotitanate, Li amide and Na methylate, the methanol formed being removed by distillation. Higher-molecular benztriazole acid esters according to the invention are formed in this way.

If n is 2 in formula I, a corresponding transesterification with dialcohols of the formula $HO-R^9-OH$ is also possible, the quantity of this dialcohol corresponding to the equation being reduced to one half.

In the preparation of compounds of the formula I containing one or more amide groups, the following procedure is followed:

5) Thermal reaction of benztriazolecarboxylic acid esters (preferably methyl or ethyl esters) if desired in the presence of catalysts, for example Li amide or Na methylate, with ammonia or a primary or secondary amine of the formula

or, if n is 2 in formula I, with diamines of the formula

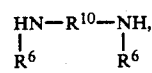

in each case distilling off the alcohol set free, in order to give the corresponding benztriazolecarboxylic acid amides.

6) The same amides can, however, also be obtained by reacting the acid chlorides, according to the invention, of the formula I, which are obtainable, for example, by reaction 3, with ammonia or a primary or secondary monoamine or diamine in the presence of an acid acceptor (for example triethylamine).

7) Incorporation of the benztriazolecarboxylic acid into lacquer binders, for example PES resins or epoxide resins.

The o-nitroanilines and 2-(3-tert.-butyl-4-hydroxyphenyl)-propionic acid which are used as starting substances for the preparation of the benztriazolecarboxylic acids according to the invention are known compounds which can also be prepared by known processes. On the other hand, the diazo dyes obtained as intermediates are novel substances.

The compounds according to the invention are effective light stabilisers for organic materials, for example for a large number of polymers. For applications in colour photographic material or in lacquers and in all cases where the use of liquid light stabilisers affords decisive advantages, the use of mixtures of products of the present invention, for example mixtures consisting of 2 or more esters, is very particularly advantageous. The stabilisers according to the invention or mixtures thereof are preferably employed in an amount of 0.1–5% by weight, in particular 0.5 to 3% by weight, relative to the organic material. The following are suitable polymers:

1. Polymers of monoolefines and diolefines, for example polyethylene (which can, if desired, be crosslinked), polypropylene, polyisobutylene, polybut-1-ene, polymethylpent-1-ene, polyisoprene or polybutadiene, and also polymers of cycloolefines, for example polymers of cyclopentene or norbornene.

2. Mixtures of the polymers mentioned uner 1), for example mixtures of polypropylene with polyethylene or with polyisobutylene.

3. Copolymers of monoolefines or diolefines with one another or with other vinyl monomers, for example ethylene/propylene copolymers, propylene/but-1-ene copolymers, propylene/isobutylene copolymers, ethylene/but-1-ene copolymers, propylene/butadiene copolymers, isobutylene/isoprene copolymers, ethylene/ethyl acrylate copolymers, ethylene/alkyl methacrylate copolymers, ethylene/vinyl acetate copolymers or ethylene/acrylic acid copolymers and salts thereof (ionomers), and also terpolymers of ethylene with propylene and a diene, such as hexadiene, dicyclopentadiene or ethylidenenorbornene.

4. Polystyrene.

5. Random copolymers of styrene or α-methylstyrene with dienes or acrylic derivatives, for example styrene/butadiene, styrene/acrylonitrile, styrene/ethyl methacrylate or styrene/acrylonitrile/methacrylate; mixtures of high impact strength obtained from styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene or styrene/ethylene-propylene/styrene.

6. Graft copolymers of styrene, for example styrene on polybutadiene, styrene and acrylonitrile on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers and mixtures thereof with the copolymers mentioned under 5), such as are known as so-called ABS, MBS, ASA or AES polymers.

7. Halogen-containing polymers, for example polychloroprene, chlorinated rubber, chlorinated or chlorosulfonated polyethylene and especially polymers formed from halogen-containing vinyl compounds, for example polyvinyl chloride, polyvinylidene chloride, polyvinyl fluoride and polyvinylidene fluoride and also copolymers thereof, such as vinyl chloride/vinylidene chloride, vinyl chloride/vinyl acetate or vinylidene chloride/vinyl acetate.

8. Polymers derived from $\alpha,\beta$-unsaturated acids and derivatives thereof, such as polyacrylates and polymethacrylates, polyacrylamides and polyacrylonitriles.

9. Copolymers of the monomers mentioned under 8) with one another or with other unsaturated monomers, for example acrylonitrile/butadiene copolymers, acrylonitrile/alkyl acrylate copolymers, acrylonitrile/vinyl chloride copolymers or acrylonitrile/alkyl methacrylate/butadiene terpolymers.

10. Polymers derived from unsaturated alcohols and amines or acyl derivatives or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine.

11. Homopolymers and copolymers of cyclic ethers, such as polyalkylene glycols, polyethylene oxide or polypropylene oxide or copolymers thereof with bisglycidyl ethers.

12. Polyacetals, such as polyoxymethylene and also polyoxymethylenes containing comonomers such as ethylene oxide.

13. Polyphenylene oxides and sulfides and also mixtures of polyphenylene oxides and polystyrene.

14. Polyurethanes derived, on the one hand, from polyethers, polyesters and polybutadienes having terminal hydroxyl groups and, on the other hand, from aliphatic or aromatic polyisocyanates, and also precursors thereof.

15. Polyamides and copolyamides derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide and poly-m-phenylene isophthalamide, and copolymers thereof with polyethers, for example copolymers with polyethylene glycol, polypropylene glycol or polytetramethylene glycol.

16. Polyureas, polyimides and polyamide-imides.

17. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates, and also block polyether-esters derived from polyethers containing hydroxyl end groups.

18. Polycarbonates.

19. Polysulfones and polyether-sulfones.

20. Crosslinked polymers derived, on the one hand, from aldehydes and, on the other hand, from phenols, urea or melamine, such as phenol-formaldehyde, urea-formaldehyde and melamine-formaldehyde resins.

21. Drying and non-drying alkyd resins.

22. Unsaturated polyester resins derived from copolyesters of saturated and unsaturated dicarboxylic acids with polyhydric alcohols, and also vinyl compounds as crosslinking agents, and also halogen-containing modifications of low combustibility.

23. Crosslinkable acrylic resins derived from substituted acrylic acid esters, for example epoxy acrylates, urethane acrylates or polyester acrylates.

24. Alkyd resins, polyester resins and acrylate resins which have been crosslinked with melamine resins, urea resins, polyisocyanates or epoxide resins.

25. Crosslinked epoxide resins derived from polyepoxides, for example from bis-glycidyl ethers or cycloaliphatic diepoxides.

26. Natural polymers, such as cellulose, natural rubber and gelatine, and also their polymer-homologously chemically modified derivatives, such as cellulose acetates, propionates and butyrates, and the cellulose ethers, such as methylcellulose.

The invention thus relates also to stabilised organic materials, in particular synthetic polymers, which preferably contain 0.1 to 5% by weight of a compound of the formula I in the material.

The compounds according to the invention are not only effective light stabilisers, like the known UV absorbers based on benztriazole, but also, by virtue of their surprisingly low loss through volatilisation at high temperature, are particularly valuable for stabilising polymers which have to be processed at high temperatures.

The compounds according to the invention are therefore preferably employed for stabilising polyesters, for example polyethylene terephthalate, polybutylene terephthalate or copolymers thereof, polycarbonates, for example those derived from bisphenol A and phosgene or copolymers thereof, polyamides, for example nylon 6, nylon 6,6, nylon 6,10 and the like and copolymers, MF and UF resins, thermoplastic acrylic resins which can be crosslinked by heat, and polyurethanes.

Appropriately stabilised compositions are thus a preferred form of the compositions which have been previously mentioned and claimed. It is preferable to stabilise lacquers formed from polymers of this type.

The stabilisers of the formula I can be incorporated into the organic material by the conventional methods, for example in any desired phase during the manufacture of shaped products. They can, for example, be mixed in the form of a liquid, a powder, suspensions or emulsions or solutions into the polymer, which can be in the form of a powder, melt, solution, suspension or emulsion.

The stabilised mixtures of the invention can, if desired, contain 0.1 to 5% by weight, preferably 0.5 to 3% by weight, relative to the polymer, of the customary additives, in particular antioxidants, light stabilisers or mixtures thereof. The following are examples of such additives:

1. ANTIOXIDANTS 1.1. Alkylated monophenols 2,6-Di-tert.-butyl-4-methylphenol, 2-tert.-butyl-4,6-dimethylphenol, 2,6-di-tert.-butyl-4-ethylphenol, 2,6-di-tert.-butyl-4-n-butylphenol, 2,6-di-tert.-butyl-4-i-butylphenol, 2,6-di-cyclopentyl-4-methylphenol, 2-($\alpha$-methylcyclohexyl)-4,6-dimethylphenol, 2,6-di-octadecyl-4-methylphenol, 2,4,6-tri-cyclohexylphenol and 2,6-di-tert.-butyl-4-methoxymethylphenol.

1.2. Alkylated hydroquinones 2,6-Di-tert.-butyl-4-methoxyphenol, 2,5-di-tert.-butylhydroquinone, 2,5-di-tert.-amylhydroquinone, and 2,6-diphenyl-4-octadecyloxyphenol.

1.3. Hydroxylated thiodiphenyl ethers 2,2'-Thio-bis-(6-tert.-butyl-4-methylphenol), 2,2'-thio-bis-(4-octylphenol), 4,4'-thio-bis-(6-tert.-butyl-3-methylphenol) and 4,4'-thio-bis-(6-tert.-butyl-2-methylphenol).

1.4. Alkylidene-bisphenols 2,2'-Methylene-bis-(6-tert.-butyl-4-methylphenol), 2,2'-methylene-bis-(6-tert.-butyl-4-ethylphenol), 2,2'-methylene-bis-[4-methyl-6-($\alpha$-methylcyclohexyl)-phenol], 2,2'-methylene-bis-(4-methyl-6-cyclohexylphenol), 2,2'-methylene-bis-(6-nonyl-4-methylphenol), 2,2'-methylene-bis-(4,6-di-tert.-butylphenol), 2,2'-ethylidene-bis-(4,6-di-tert.-butylphenol), 2,2'-ethylidene-bis-(6-tert.-butyl-4-isobutylphenol), 4,4'-methylene-bis-(2,6-di-tert.-butylphenol), 4,4'-methylene-bis-(6-tert.-butyl-2-methylphenol), 1,1-bis-(5-tert.-butyl-4-hydroxy-2-methylphenyl)-butane, 2,6-di-(3-tert.-butyl-5-methyl-2-hydroxybenzyl)-4-methylphenol, 1,1,3-tris-(5-tert.-butyl-4-hydroxy-2-methylphenyl)-butane, 1,1-bis-(5-tert.-butyl-4-hydroxy-2-methylphenyl)-3-n-dodecylmercaptobutane, ethylene glycol bis-[3,3-bis-(3'-tert.-butyl-4'-hydroxyphenyl)-butyrate], di-(3-tert.-butyl-4-hydroxy-5-methylphenyl)-dicyclopentadiene and di-[2-(3'-tert.-butyl-2'-hydroxy-5'-methylbenzyl)-6-tert.-butyl-4-methylphenyl] terephthalate.

1.5. Benzyl compounds 1,3,5-Tri-(3,5-di-tert.-butyl-4-hydroxybenzyl)-2,4,6-trimethylbenzole, di-(3,5-di-tert.-butyl-4-hydroxybenzyl) sulfide, isooctyl 3,5-di-tert.-butyl-4-hydroxybenzylmercaptoacetate, bis-(4-tert.-butyl-3-hydroxy-2,6-dimethylbenzyl)-dithiol terephthalate, 1,3,5-tris-(3,5-di-tert.-butyl-4-hydroxybenzyl) isocyanurate, 1,3,5-tris-(4-tert.-butyl-3-hydroxy-2,6-dimethylbenzyl) isocyanurate, di-octadecyl 3,5-di-tert.-butyl-4-hydroxybenzylphosphonate and the calcium salt of monoethyl 3,5-di-tert.-butyl-4-hydroxybenzylphosphonate.

1.6. Acylaminophenols

4-Hydroxylauric acid anilide, 4-hydroxystearic acid anilide and 2,4-bis-octylmercapto-6-(3,5-di-tert.-butyl-4-hydroxyanilino)-S-triazine.

1.7. Esters of $\beta$-(3,5-di-tert.-butyl-4-hydroxyphenyl)-propionic acid with monohydric or polyhydric alcohols, for example with:

Methanol, octadecanol, 1,6-hexanediol, neopentylglycol, thiodiethylene glycol, diethylene glycol, triethylene glycol, pentaerythritol, tris-hydroxyethyl isocyanurate and di-hydroxyethyl oxalic acid diamide.

1.8. Esters of $\beta$-(5-tert.-butyl-4-hydroxy-3-methylphenyl)-propionic acid with monohydric or polyhydric alcohols, for example with:

Methanol, octadecanol, 1,6-hexanediol, neopentylglycol, thiodiethylene glycol, diethylene glycol, triethylene glycol, pentaerythritol, tris-hydroxyethyl isocyanurate and di-hydroxyethyl oxalic acid diamide.

1.9. Amides of $\beta$-(3,5-di-tert.-butyl-4-hydroxyphenyl)-propionic acid, for example:

N,N'-di-(3,5-di-tert.-butyl-4-hydroxyphenylpropionyl)-hexamethylenediamine, N,N'-di-(3,5-di-tert.-butyl-4-hydroxyphenylpropionyl)-trimethylenediamine and N,N'-di-(3,5-di-tert.-butyl-4-hydroxyphenylpropionyl)-hydrazine.

2. UV ABSORBERS AND LIGHT STABILISERS 2.1. 2-(2'-Hydroxyphenyl)-benztriazoles, for example: the 5'-methyl-, 3',5'-di-tert.-butyl-, 5'-tert.-butyl, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 4'-octoxy-and 3',5'-di-tert.-amyl-derivative.

2.2. 2-Hydroxybenzophenones, for example: the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxyderivative.

2.3. Esters of substituted or unsubstituted benzoic acids, for example:

4-tert.-butylphenyl salicylate, phenyl salicylate, octylphenyl salicylate, dibenzoylresorcinol, bis-(4-tert.- butylbenzoyl)-resorcinol, benzoylresorcinol and 2,4-di-tert.-butylphenyl 3,5-di-tert.-butyl-4-hydroxybenzoate.

2.4. Acrylates, for example:

ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example:

nickel complexes of 2,2'-thio-bis-[4-(1,1,3,3-tetramethylbutyl)-phenols], such as the 1:1 or 1:2 complexes, if desired containing additional ligands, such as n-butylamine, triethanolamine or N-cyclohexyldiethanolamine, nickel dibutyldithiocarbamate, nickel salts of 4-hydroxy-3,5-di-tert.-butylbenzylphosphonic acid monoalkyl esters, such as the methyl or ethyl ester, nickel complexes of ketoximes, such as 2-hydroxy-4-methylphenylundecylketone oxime and nickel complexes of 1-phenyl-4-lauroyl-5-hydroxypyrazole, if desired containing additional ligands.

2.6. Sterically hindered amines, for example:

bis-(2,2,6,6-tetramethylpiperidyl) sebacate, bis-(1,2,2,6,6-pentamethylpiperidyl) sebacate, bis-(1,2,2,6,6-pentamethylpiperidyl) n-butyl-3,5-di-tert.-butyl-4-hydroxybenzylmalonate, the condensation product formed from 1-hydroxyethyl-2,2,6,6-tetramethyl-4-hydroxypiperidine and succinic acid, the condensation product formed from N,N'-(2,2,6,6-tetramethylpiperidyl)-hexamethylenediamine and 4-tert.-octylamino-2,6-dichloro-1,3,5-s-triazine, and tris-(2,2,6,6-tetramethylpiperidyl) nitrilotriacetate.

2.7. Oxalic acid diamides, for example:

4,4'-di-octyloxyoxanilide, 2,2'-di-octyloxy-5,5'-di-tert.-butyl-oxanilide, 2,2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyl-oxanilide and a mixture thereof with 2-ethoxy-2'-ethyl-5,4'-di-tert.-butyl-oxanilide and mixtures of ortho-methoxy and para-methoxy and of o-ethoxy and p-ethoxy-disubstituted oxanilides.

3. Metal deactivators, for example:

N,N'-diphenyloxalic acid diamide, N-salicylal-N'-salicyloylhydrazine, N,N'-bis-salicyloylhydrazine, N,N'-bis-(3,5-di-tert.-butyl-4-hydroxyphenylpropionyl)-hydrazine, 3-salicyloylamino-1,2,4-triazole and bis-benzylideneoxalic acid dihydrazide.

4. Phosphites and phosphonites, for example:

triphenyl phosphite, diphenyl alkyl phosphites, phenyl dialkyl phosphites, tri-(nonylphenyl) phosphite, trilauryl phosphite, trioctadecyl phosphite, distearyl pentaerythritol diphosphite, tris-(2,4-di-tert.-butylphenyl) phosphite, diisodecyl pentaerythritol diphosphite, di-(2,4-di-tert.-butylphenyl) pentaerythritol diphosphite, tristearyl sorbitol triphosphite and tetrakis-(2,4-di-tert.-butylphenyl) 4,4'-biphenylene-diphosphonite.

5. Compounds which destroy peroxide, for example:

esters of β-thio-dipropionic acid, for example the lauryl, stearyl, myristyl or tridecyl ester, mercaptobenzimidazole, the zinc salt of 2-mercaptobenzimidazole, zinc dibutyldithiocarbamate, dioctadecyl disulfide and pentaerythritol tetrakis-(β-dodecylmercapto)-propionate.

6. Polyamide stabilisers, for example:

copper salts in combination with iodides and/or phosphorus compounds and salts of divalent manganese.

7. Basic co-stabilisers, for example:

melamine, polyvinylpyrrolidone, dicyandiamide, triallyl cyanurate, urea derivatives, hydrazine derivatives, amines, polyamides, polyurethanes, alkali metal and alkaline earth metal salts of higher fatty acids, for example Ca stearate, Zn stearate, Mg stearate, Na ricinoleate and K palmitate, antimony pyrocatecholate or tin pyrocatecholate.

8. Nucleating agents, for example:

4-tert.-butylbenzoic acid, adipic acid or diphenylacetic acid.

9. Fillers and reinforcing agents, for example:

calcium carbonates, silicates, glass fibres, asbestos, talc, kaolin, mica, barium sulfate, metal oxides and hydroxides, carbon black and graphite.

10. Miscellaneous additives, for example:

plasticisers, lubricants, emulsifiers, pigments, fluorescent brighteners, flameproofing agents, antistatic agents and blowing agents.

The stabilisation of thermosetting and thermoplastic acrylic resins which are used for automobile finishes is of particular interest. These substances are described in "Encyclopedia of Polymer Science and Technology", Interscience Publishers, New York, Volume 1 (1964), on pages 273 to 276 and Volume 13 (1970), on pages 530 to 532, and also in "Understanding Paint" by W. R. Fuller in American Paint Journal, St. Louis, 1965, pages 124 to 135.

Acrylic resin lacquers which are stabilised in accordance with the invention against the action of light, oxygen and moisture are the customary stoving lacquers, for example those described in H. Kittel's "Lehrbuch der Lacke und Beschichtungen" ("Textbook of Lacquers and Coatings"), Volume 1, Part 2, pages 735 and 742 (Berlin, 1972), and in H. Wagner, H. F. Sarx, "Lackkunstharze" ("Synthetic Resins for Lacquers"), pages 229 to 235.

The stabilisation, by means of the compounds according to the invention, of metal effect lacquers based on an acrylic resin which can be crosslinked by heat is of particular interest. An unstabilised metal effect lacquer prepared from these resins is unsuitable, in spite of its excellent physical and chemical properties, since the UV light can pass unhindered through the top coat and leads to cracking in the coat below. Other lacquers and coatings which can be crosslinked by heat and are based on acrylic resins, melamine resins, alkyd resins, polyester resins, epoxy resins or mixtures thereof, can also be stabilised effectively by means of the compounds according to the invention.

In order to achieve the metal effect, the conventional aluminium pigments are used in a concentration of 1 to 10% by weight, relative to solvent-free binder (lacquer resin). The stabilised lacquers can be applied by the conventional one-coat or two-coat processes. In the latter case the initial lacquer containing the pigment is first applied and is then overlaid with transparent lacquer.

Further additives which can be present in the lacquer are other customary light stabilisers, phenolic antioxidants, pigments, dyes, metal deactivators and the like.

A particularly effectively stabilised lacquer is constituted by one of the following composition:

a) an acrylic resin which can be crosslinked by heat and b) 0.1 to 5% by weight, relative to the resin, of a compound of the formula I or of a mixture of compounds of the formula I, and c) 0.1 to 5% by weight, relative to the resin, of a stearically hindered amine stabiliser.

The lacquer preferably contains 0.5 to 2% by weight, relative to the resin, of the component b) and 0.5 to 2% by weight, relative to the resin, of the component c).

Examples of suitable sterically hindered amines are amines such as are described in German Offenlegungschrift No. 2,500,134, in U.S. Pat. No. 4,110,304 or in the "Taschenbuch der Kunststoff-Additive" ("Pocketbook of Plastics Additives") by R. Gächter and H. Müller (Hanser Verlag, Munich, 1979). Bis-(1,2,2,6,6-pentamethyl-4-piperidyl) sebacate or bis-(1,2,2,6,6-pentamethyl-4-piperidyl) 2-n-butyl-2-(3,5-di-tert.-butyl-4-hydroxybenzyl)-malonate are particularly suitable.

The combination of sterically hindered amines and the stabilisers according to the invention makes possible excellent retention of gloss when exposed to weathering as well as resistance to flaking in metallised stoving lacquers for the application of automobile top lacquers.

The compounds, according to the invention, of the formula I differ in four outstanding properties from the benztriazole compounds of the state of the art which are closely related structurally. These compounds 1. are sparingly volatile,
2. are readily soluble in the solvents used for plastics coatings,
3. have improved compatibility with polyolefines or vinyl polymers, and
4. exhibit a low tendency to crystallise, in particular when employed as mixtures.

Their sparing volatility, in particular when combined with good compatibility with the substrate and solubility, makes it possible to incorporate the compounds according to the invention without problems into the polymer, where they remain, even after processing at high temperature, and thus impart the desired stability to the end product.

The greater compatibility with the substrate of the compounds according to the invention, together with the sparing volatility already discussed, makes it possible to process and use the stabilised products at elevated temperatures and also makes possible a prolonged period of use of the products at customary temperatures. This prevents the undesirable exudation of the stabiliser during processing, which otherwise frequently leads to expensive damage to the production equipment.

The invention also relates further to stabilised organic material which is in the form of photographic material or is part of a photographic material, the photographic material containing, preferably in top layers, 0.1 to 5% by weight, relative to the photographic material without stabiliser, of a compound according to the invention.

The examples which follow illustrate the invention.

EXAMPLE 1

37.1 g of azo dye (melting point 201° C.), obtained by coupling diazotised o-nitroaniline with 2-(3-tert.-butyl-4-hydroxyphenyl)-propionic acid, are introduced into 200 ml of 2N sodium hydroxide solution. 30 g of zinc dust are added to the mixture and 50 ml of 10N sodium hydroxide solution are then added dropwise in the course of one hour, the temperature being kept below 45° C. The mixture is then warmed at 85° to 90° C. for 1 hour, the zinc sludge is filtered off at this temperature and the filtrate is acidified with concentrated hydrochloric acid. The precipitate which is thus deposited is filtered off, washed with water, dried and recrystallised from ligroin. This gives 2-[2-hydroxy-3-tert.-butyl-5-(2-carboxyethyl)-phenyl]-benztriazole (compound 1), melting point 195° C.

The procedure described above is repeated, using the azo dye (melting point 192° C.) obtained by coupling diazotised p-chloro-o-nitroaniline with 2-(3-tert.-butyl-4-hydroxyphenyl)-propionic acid instead of the abovementioned azo dye. 2-[2-Hydroxy-3-tert.-butyl-5-(2-carboxyethyl)-phenyl]-5-chlorobenztriazole (compound 2), melting point 192° C., is obtained.

EXAMPLE 2

33.9 g of 2-[2-hydroxy-3-tert.-butyl-5-(2-carboxyethyl)-phenyl]-benztriazole (compound 1) are suspended in 200 ml of toluene. After adding 2 ml of dimethylformamide and 20 g of thionyl chloride, the reaction mixture is warmed slowly to 80° C. and is stirred at this temperature until the evolution of sulfur dioxide and hydrochloric acid ceases. Excess thionyl chloride and toluene are then distilled off in vacuo and the resulting residue is recrystallised from hexane. This gives 2-[2-hydroxy-3-tert.-butyl-5-(2-chlorocarbonylethyl)-phenyl]-benztriazole (compound 3), melting point 104° to 106° C.

Exactly the same procedure is repeated using 2-[2-hydroxy-3-tert.-butyl-5-(2-carboxyethyl)-phenyl]-5-chlorobenztriazole. 2-[2-Hydroxy-3-tert.-butyl-5-(2-chlorocarbonylethyl)-phenyl]-5-chlorobenztriazole (compound 4), melting point 102° to 105° C., is obtained.

EXAMPLE 3

33.9 g of 2-[2-hydroxy-3-tert.-butyl-5-(2-carboxyethyl)-phenyl]-benztriazole (compound 1) in 150 ml of methanol and 1 ml of concentrated sulfuric acid are boiled under reflux for 3 hours. On cooling the reaction solution, 2-[2-hydroxy-3-tert.-butyl-5-(2-carbomethoxyethyl)-phenyl]-benztriazole (compound 5), melting point 121° to 122° C., crystallises out.

Exactly the same procedure is repeated using 2-[2-hydroxy-3-tert.-butyl-5-(2-carboxyethyl)-phenyl]-5-chlorobenztriazole (compound 2). 2-[2-Hydroxy-3-tert.-butyl-5-(2-carbomethoxyethyl)-phenyl]-5-chlorobenztriazole (compound 6), melting point 112° to 113° C., is obtained.

An equal quantity of ethanol, n-butanol, isobutanol, allyl alcohol or chloropropanol is used instead of methanol and the reaction mixture is reacted with 1 ml of concentrated sulfuric acid for approx. 3-6 hours at a temperature of 70°-75° C. and is evaporated on a rotary evaporator, and the residue is crystallised from hexane or ligroin. The following are then obtained: 2-[2-hydroxy-3-tert.-butyl-5-(2-carboethoxyethyl)-phenyl]-benztriazole. Melting point: 96°-98° C. (compound 7). 2-[2-Hydroxy-3-tert.-butyl-5-(2-carboethoxyethyl)-phenyl]-5-chlorobenztriazole. Melting point: 100°-101° C. (compound 8). 2[2-Hydroxy-3-tert.-butyl-5-(2-carbo-n-butoxyethyl)-phenyl]-benztriazole. Melting point: 55°-57° C. (compound 9). 2-[2-Hydroxy-3-tert.-butyl-5-(2-carbo-n-butoxyethyl)-phenyl]-5-chlorobenztriazole. Melting point: 63°-64° C. (compound 10). 2-[2-Hydroxy-3-tert.-butyl-5-(2-carbo-isobutoxyethyl)-phenyl]-benztriazole. Melting point: 86°-87° C. (compound 11). 2-[2-Hydroxy-3-tert.-butyl-5-(2-carbo-isobutoxyethyl)-phenyl]-5-chlorobenztriazole. Melting point: 90°-91° C. (compound 12). 2-[2-Hydroxy-3-tert.-butyl-5-(2-carboallyloxyethyl)-phenyl]-benztriazole. Melting point: 120°-121° C. (compound 13). 2-[2-

Hydroxy-3-tert.-butyl-5-(2-carbo-γ-chloropropoxyethyl)-phenyl]-benztriazole. Melting point: 82°–84° C. (compound 14).

EXAMPLE 4

35.3 g of 2-[2-hydroxy-3-tert.-butyl-5-(2-carbomethoxyethyl)-phenyl]-benztriazole (compound 5) are stirred in 200 ml of xylene with 12 g of cyclohexanol and 1 g of tetrabutyl orthotitanate for approx. 12 hours at 130° C. until methanol no longer distils off. After cooling to room temperature, the reaction solution is extracted by shaking with 200 ml of saturated, aqueous sodium bicarbonate solution, washed with water, dried over sodium sulfate and evaporated in vacuo. Crystallising the residue from evaporation from hexane gives 2-[2-hydroxy-3-tert.-butyl-5-(2-carbocyclohexyloxyethyl)-phenyl]-benztriazole (compound 15), melting point 86° to 87° C.

The procedure described above is repeated, using a corresponding amount of n-octanol, 2-ethylhexanol, isodecanol or n-dodecanol instead of cyclohexanol. The following are obtained, respectively: 2-[2-hydroxy-3-tert.-butyl-5-(2-carbooctyloxyethyl)-phenyl]-benztriazole (compound 16) in the form of a yellowish resin which solidifies in the course of time to give a wax-like mass, 2-{2-hydroxy-3-tert.-butyl-5-[2-carbo-(2-ethylhexyloxy)-ethyl}-benztriazole (compound 17) in the form of a slightly yellow, viscous resin, 2-[2-hydroxy-3-tert.-butyl-5-(2-carbo-iso-decyloxyethyl)-phenyl]-benztriazole (compound 18) in the form of a slightly yellowish resin or 2-[2-hydroxy-3-tert.-butyl-5-(2-carbodecyloxyethyl)-phenyl]-benztriazole (compound 19), melting point 51° to 52° C.

EXAMPLE 5

37.4 g of 2-[2-hydroxy-3-tert.-butyl-5-(2-carboxyethyl)-phenyl]-5-chlorobenztriazole (compound 2) in 400 ml of toluene are boiled with 20 g of 1-dodecanol and 2 ml of phosphoric acid for 12 hours under a water separator. After cooling, the reaction solution is washed with water until it is neutral and is then evaporated in vacuo. Recrystallising the residue from evaporation from isopropanol gives 2-[2-hydroxy-3-tert.-butyl-5-(2-carbododecyloxyethyl)-phenyl]-5-chlorobenztriazole (compound 20), melting point 55° to 56° C.

The above procedure is repeated, using a corresponding amount of a) 1-octanol, b) 2-ethylhexanol, c) glycerol, d) cyclohexanol, e) triethylene glycol, f) tert.-amyl alcohol, g) hexanediol or h) cyclohexyl carbinol instead of 1-dodecanol. The following products are obtained:

a) 2-[2-hydroxy-3-tert.-butyl-5-(2-carbooctyloxyethyl)phenyl]-5-chlorobenztriazole (compound 21), b) 2-{2-hydroxy-3-tert.-butyl-5-[2-carbo-(2-ethylhexyloxy)-ethyl]-phenyl}-5-chlorobenztriazole (compound 22), c) a compound of the formula

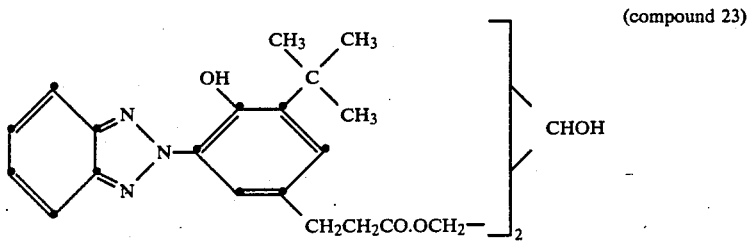

(compound 23)

(glassy resin; solidification point 94°–97° C.), d) 2-[2-hydroxy-3-tert.-butyl-5-(2-carbocyclohexyloxyethyl)-phenyl]-5-chlorobenztriazole (compound 24); melting point 84°–86° C. (hexane), e) a compound of the formula

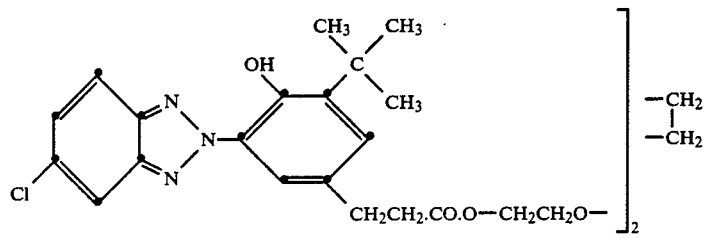

(compound 25) melting point 103°–105° C. (toluene), f) 2-[2-hydroxy-3-tert.-butyl-5-(2-carbo-tert.-amyloxyethyl)-phenyl]-benztriazole; melting point 101°–103° C. (hexane); (compound 26), 2-[2-hydroxy-3-tert.-butyl-5-(2-carbo-tert.-amyloxyethyl)-phenyl]-chlorobenztriazole; melting point 94°–95° C. (compound 27), g) 2-[2-hydroxy-3-tert.-butyl-5-(2-carbo-(6-hydroxyhexyloxy)-ethyl)-phenyl]-benztriazole; melting point 57°–59° C.; (compound 29), 2-[2-hydroxy-3-tert.-butyl-5-(2-carbo-(6-hydroxyhexyloxy)ethyl)-phenyl]-chlorobenztriazole, a resin (compound 30).

| Elementary analysis: | |
|---|---|
| Calculated: C = 63.50% | Found: C = 63.56% |
| H = 6.80% | H = 6.97% |
| N = 8.87% | N = 8.95% |
| Cl = 7.48% | Cl = 7.33% | h) 2-[2-hydroxy-3-tert.-butyl-5-(2-carbocyclohexylmethoxyethyl)-phenyl]-5-chlorobenztriazole; melting point 100°–101° C. (compound 28).

If the hexanediol reacts twice, the following are obtained:

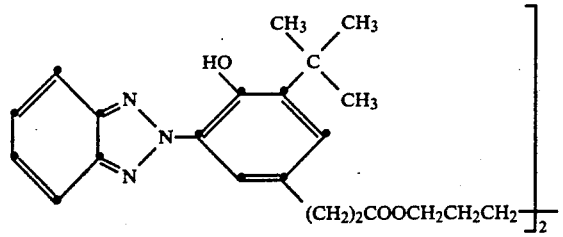

Melting point: 106–108° C.
(ethyl acetate)
(compound 31)

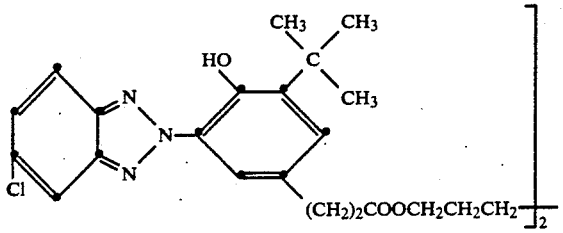

Melting point: 91–93° C.
(hexane)
(compound 32).

EXAMPLE 6

33.9 g of 2-[2-hydroxy-3-tert.-butyl-5-(2-carboxyethyl)-phenyl]-benztriazole (compound 1) in 300 ml of xylene are boiled under reflux with 9.0 g of cyclohexene oxide for 12 hours under nitrogen. The solvent is evaporated in vacuo and the residue is crystallised from ligroin. This gives 2-{2-hydroxy-3-tert.-butyl-5-[2-carbo-(2-hydroxycyclohexyloxy)-ethyl]-phenyl}-benztriazole (compound 33), melting point 118° to 119° C.

The above procedure is repeated, using the epoxides and glycidyl compounds shown below instead of cyclohexene oxide. The benztriazoles shown are obtained:

Epichlorohydrin:
2-[2-Hydroxy-3-tert.-butyl-5-(2-carbo-(2-hydroxy-3-chloropropoxy)-ethyl)-phenyl]-benztriazole. Melting point: 69°–71° C. (cyclohexane) (compound 34).

2-[2-Hydroxy-3-tert.-butyl-5-(2-carbo-(2-hydroxy-3-chloropropoxy)-ethyl)-phenyl]-5-chlorobenztriazole. Melting point: 90°–92° C. (cyclohexane) (compound 35).

Butyl glycidyl ether:
2-[2-Hydroxy-3-tert.-butyl-5-(2-carbo-(2-hydroxy-4-oxaoctyloxy)-ethyl)-phenyl]-benztriazole. Melting point: 42°–43° C. (ligroin) (compound 36).

2-[2-Hydroxy-3-tert.-butyl-5-(2-carbo-(2-hydroxy-4-oxaoctyloxy)-ethyl)-phenyl]-5-chlorobenztriazole. Resin (compound 37).

| Elementary analysis: | |
|---|---|
| Calculated: C = 61.71% | Found: C = 61.91% |
| H = 7.17% | H = 6.83% |
| N = 8.30% | N = 8.31% |
| Cl = 7.01% | Cl = 7.27% |

Allyl glycidyl ether:
2-[2-Hydroxy-3-tert.-butyl-5-(2-carbo-(2-hydroxy-3-allyloxypropoxy)-ethyl)-phenyl]-benztriazole. Melting point: 52°–53° C. (hexane) (compound 38).

2-[2-Hydroxy-3-tert.-butyl-5-(2-carbo-(2-hydroxy-3-allyloxypropoxy)-ethyl)-phenyl]-5-chlorobenztriazole. Resin (compound 39).

| Elementary analysis: | |
|---|---|
| Calculated: C = 61.53% | Found: C = 61.60% |
| H = 6.20% | H = 6.11% |
| N = 8.61% | N = 8.71% |
| Cl = 7.26% | Cl = 7.40% |

Cyclohexyl glycidyl ether:
2-[2-Hydroxy-3-tert.-butyl-5-(2-carbo-(2-hydroxy-4-cyclohexyl-4-oxabutoxy)-ethyl)-phenyl]-benztriazole. Melting point: 69°–70° C. (compound 40).

2-[2-Hydroxy-3-tert.-butyl-5-(2-carbo-(2-hydroxy-4-cyclohexyl-4-oxabutoxy)-ethyl)-phenyl]-5-chlorobenztriazole. Resin (compound 41).

| Elementary analysis: | |
|---|---|
| Calculated: C = 63.45% | Found: C = 63.75% |
| H = 6.85% | H = 6.81% |
| N = 7.93% | N = 8.00% |
| Cl = 6.69% | Cl = 7.01% |

Styrene oxide:
2-[2-Hydroxy-3-tert.-butyl-5-(2-carbo-(2-hydroxy-2-phenylethoxy)-ethyl)-phenyl]-benztriazole. Melting point: 103°–105° C. (acetonitrile) (compound 42).

Phenyl glycidyl ether:
2-[2-Hydroxy-3-tert.-butyl-5-(2-carbo-(2-hydroxy-3-phenoxypropoxy)-ethyl)-phenyl]-benztriazole. Melting point: 99°–100° C. (compound 43).

2-tert.-Butylphenyl glycidyl ether:
2-[2-Hydroxy-3-tert.-butyl-5-(2-carbo-(2-hydroxy-3-(2-tert.-butylphenyl)-oxy-propoxy)-ethyl)-phenyl]-benztriazole. Melting point: 54°–55° C. (acetonitrile) (compound 44).

4-Phenoxyphenyl glycidyl ether:
2-[2-Hydroxy-3-tert.-butyl-5-(2-carbo-(2-hydroxy-3-(4-phenoxyphenyl)-oxy-propoxy)-ethyl)-phenyl]-benztriazole. Melting point: 73°–74° C. (hexane) (compound 45).

4-(1-Methyl-1-phenylethyl)-phenyl glycidyl ether:
2-[2-Hydroxy-3-tert.-butyl-5-(2-carbo-(2-hydroxy-3-(4-(1-methyl-1-phenylethyl)-phenyl)-propoxy)-ethyl)-phenyl]-benztriazole. Glassy resin, solidification point: 43°–48°C. (compound 46).

Octyl glycidyl ether:
2-[2-Hydroxy-3-tert.-butyl-5-(2-carbo-(2-hydroxy-3-octyloxypropoxy)-ethyl)-phenyl]-5-chlorobenztriazole. Resin (compound 47).

| Elementary analysis: | |
|---|---|
| Calculated: C = 64.32% | Found: C = 64.42% |
| H = 7.56% | H = 7.28% |
| N = 7.50% | N = 7.32% |
| Cl = 6.33% | Cl = 6.60% |

2-Ethylhexyl glycidyl ether:
2-[2-Hydroxy-3-tert.-butyl-5-(2-carbo-(2-hydroxy-3-(2-ethylhexyloxy)-propoxy)-ethyl)-phenyl]-5-chlorobenztriazole. (Compound 48) resin.

| Elementary analysis: | |
|---|---|
| Calculated: C = 64.32% | Found: C = 64.42% |

-continued

| Elementary analysis: | |
|---|---|
| H = 7.56% | H = 7.49% |
| N = 7.50% | N = 7.64% |
| Cl = 6.33% | Cl = 6.83% |

Butanediol diglycidyl ether:

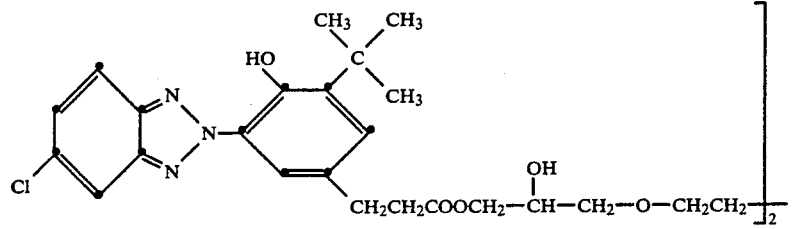

glassy resin, solidification point: 58°–62° C. (compound 49).

Bisphenol A diglycidyl ether

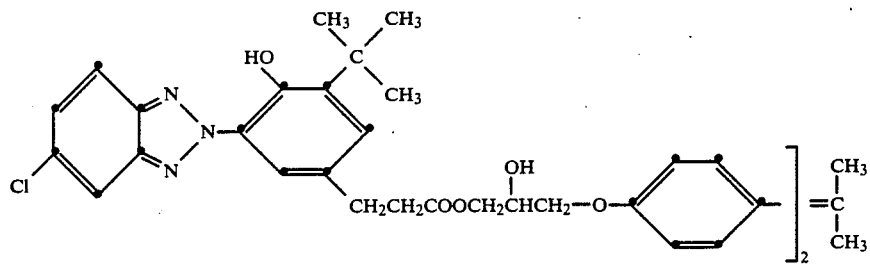

glassy resin, solidification point: 72°–76° C. (compound 50).

EXAMPLE 7

10.0 g of piperidine and 12.0 g of triethylamine are dissolved in 200 ml of toluene. A solution of 35.8 g of 2-[2-hydroxy-3-tert.-butyl-5-(2-chlorocarbonylethyl)-phenyl]-benztriazole in 100 ml of toluene is added dropwise to this solution at 20° to 25° C. in the course of approx. 30 minutes, while stirring well. Stirring is then continued for 1 hour at 35° to 40° C. and the reaction solution is then extracted with three times 200 ml of water. The toluene solution is evaporated in vacuo and the residue is crystallised from ligroin. This gives 2-[2-hydroxy-3-tert.-butyl-5-(2-carbopiperidylamidoethyl)-phenyl]-benztriazole (compound 51), melting point 102° to 104° C.

The procedure described above is repeated, using an equivalent amount of morpholine or 2,6-di-tert.-butyl-4-aminophenol instead of piperidine. 2-[2-Hydroxy-3-tert.-butyl-5-(2-carbomorpholinoamidoethyl)-phenyl]-benztriazole (compound 52), melting point 177° to 179° C., or 2-{2-hydroxy-3-tert.-butyl-5-[2-carbo-(3,5-di-tert.-butyl-4-hydroxyanilido)-ethyl]-phenyl}-benztriazole (compound 53), melting point 217° to 219° C., are obtained, respectively.

If piperazine is used,

Melting point 265–266° C. (xylene) (compound 54)

is obtained; if diisooctylamine is used,

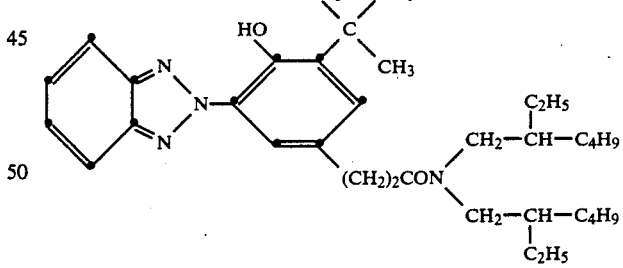

resin (compound 55) is obtained.

| Elementary analysis: | |
|---|---|
| Calculated: C = 74.69% | Found: C = 74.74% |
| H = 9.67% | H = 9.64% |
| N = 9.96% | N = 10.11% |

If morpholine is used and is reacted with 2-[2-hydroxy-3-tert.-butyl-5-(2-chlorocarbonylethyl)-phenyl]-5-chlorobenztriazole, 2-[2-hydroxy-3-tert.-butyl-5-(2-carbomorpholinoamidoethyl)-phenyl]-5-chlorobenztriazole, melting point: 159°–160° C. (cyclohexane) (compound 56), is obtained.

EXAMPLE 8

33.9 g of 2-[2-hydroxy-3-tert.-butyl-5-(2-carboxyethyl)-phenyl]-benztriazole are suspended in 100 ml of ethylene glycol monomethyl ether, 1 ml of concentrated sulfuric acid is added and the mixture is warmed at 70°–75° C. for approx. 20 hours, while stirring. A brownish-yellow clear solution is formed after a short time. When the reaction time is complete, the whole solution is poured into approx. 1.5 l of distilled water and the mixture is extracted with ethyl acetate. The organic phase is washed again twice with distilled water (or with 5% potassium carbonate solution if a little unreacted benztriazolecarboxylic acid is still present), dried with anhydrous sodium sulfate and evaporated. The residue is recrystallised from ligroin. This gives 2-[2-hydroxy-3-tert.-butyl-5-(2-carbo-(2-methoxyethoxy)-ethyl)-phenyl]-benztriazole. Melting point: 86°–87° C. (compound 57).

The above procedure is repeated, using the corresponding "chlorobenztriazolecarboxylic acid" for the esterification. The following compound, 2-[2-hydroxy-3-tert.-butyl-5-(2-carbo-(2-methoxyethoxy)-ethyl)-phenyl]-5-chlorobenztriazole is obtained. Melting point: 66°–67° C. (compound 58).

Exactly the same procedure as described above is repeated, using: a) ethylene glycol monoethyl ether or b) ethylene glycol monobutyl ether or c) diethylene glycol monoethyl ether or d) diethylene glycol monobutyl ether, instead of ethylene glycol monomethyl ether. Novel benztriazoles which are in some cases liquid, viscous oils and in some cases only crystallise after weeks or months are obtained.

a) 2-[2-Hydroxy-3-tert.-butyl-5-(2-carbo-(2-ethoxythoxy)-ethyl)-phenyl-benztriazole. Melting point: 53°–54° C. (compound 59).

2-[2-Hydroxy-3-tert.-butyl-5-(2-carbo-(2-ethoxythoxy)-ethyl)-phenyl]-5-chlorobenztriazole. Melting point: 45°–47° C. (compound 60).

b) 2-[2-Hydroxy-3-tert.-butyl-5-(2-carbo-(2-butoxythoxy)-ethyl)-phenyl]-benztriazole. Liquid oil (compound 61).

| Elementary analysis (EA): | |
|---|---|
| Calculated: C = 68.31% | Found: C = 68.31% |
| H = 7.57% | H = 7.60% |
| N = 9.56% | N = 9.52% |

2-[2-Hydroxy-3-tert.-butyl-5-(2-carbo-(2-butoxythoxy)-ethyl)-phenyl]-5-chlorobenztriazole. Yellowish oil (compound 62).

| Elementary analysis: | |
|---|---|
| Calculated: C = 63.35% | Found: C = 63.1% |
| H = 6.81% | H = 6.7% |
| N = 8.86% | N = 9.0% |
| Cl = 7.48% | Cl = 7.6% | c) 2-[2-Hydroxy-3-tert.-butyl-5-(2-carbo-(3,6-dioxaoctyloxy)-ethyl)-phenyl]-benztriazole. Melting point: 42°–44° C. (compound 63).

2-[2-Hydroxy-3-tert.-butyl-5-(2-carbo-(3,6-dioxaoctyloxy)-ethyl)-phenyl]-5-chlorobenztriazole. Yellowish oil (compound 64).

| Elementary analysis: | |
|---|---|
| Calculated: C = 61.28% | Found: C = 61.27% |
| H = 6.58% | H = 6.63% |
| N = 8.58% | N = 8.69% |
| Cl = 7.23% | Cl = 7.27% | d) 2-[2-Hydroxy-3-tert.-butyl-5-(2-carbo-(3,6-dioxadecyloxy)-ethyl)-phenyl]-benztriazole. Melting point: 42°–44° C. (compound 65).

2-[2-Hydroxy-3-tert.-butyl-5-(2-carbo-(3,6-dioxadecyloxy)-ethyl)-phenyl]-5-chlorobenztriazole. Yellowish, viscous oil (compound 66).

| Elementary analysis: | |
|---|---|
| Calculated: C = 62.60% | Found: C = 62.70% |
| H = 7.00% | H = 7.19% |
| N = 8.11% | N = 8.00% |
| Cl = 6.84% | Cl = 7.05% | using e) triethylene glycol
2-[2-Hydroxy-3-tert.-butyl-5-(2-carbo-(8-hydroxy-3,6-dioxaoctyloxy)-ethyl)-phenyl]-benztriazole. Yellow resin (compound 67).

| Elementary analysis: | |
|---|---|
| Calculated: C = 63.68% | Found: C = 63.80% |
| H = 7.05% | H = 7.09% |
| N = 8.91% | N = 9.12% |

2-[2-Hydroxy-3-tert.-butyl-5-(2-carbo-(8-hydroxy-3,6-dioxaoctyloxy)-ethyl)-phenyl]-5-chlorobenztriazole. Yellow oil (compound 68).

| Elementary analysis: | |
|---|---|
| Calculated: C = 59.34% | Found: C = 59.42% |
| H = 6.37% | H = 6.51% |
| N = 8.30% | N = 8.50% |
| Cl = 7.01% | Cl = 7.00% |

Using f) diethylene glycol
2-[2-Hydroxy-3-tert.-butyl-5-(2-carbo-(6-hydroxy-3-oxahexyloxy)-ethyl)-phenyl]-benztriazole. Melting point: 74°–76° C. (compound 69)

2-[2-Hydroxy-3-tert.-butyl-5-(2-carbo-(12-hydroxy-3,6,9-trioxadodecyloxy)-ethyl)-phenyl]-benztriazole. Yellow oil (compound 70).

| Elementary analysis: | |
|---|---|
| Calculated: C = 62.90% | Found: C = 63.15% |
| H = 7.28% | H = 7.31% |
| N = 8.15% | N = 8.43% |

Using g) tetraethylene glycol
2-[2-Hydroxy-3-tert.-butyl-5-(2-carbo-(12-hydroxy-3,6,9-trioxadodecyloxy)-ethyl)-phenyl]-5-chlorobenztriazole. Viscous oil (compound 71).

| Elementary analysis: | |
|---|---|
| Calculated: C = 58.96% | Found: C = 58.98% |
| H = 6.60% | H = 6.86% |
| N = 7.64% | N = 7.88% |
| Cl = 6.44% | Cl = 6.47% |

EXAMPLE 9

35.3 g of 2-[2-hydroxy-3-tert.-butyl-5-(2-carbomethoxyethyl)-phenyl]-benztriazole (compound 5) are melted by heating to 130° C. 20 ml of 2-ethylhexylamine (approx. 50% excess of the equivalent quantity) are added slowly under a stream of $N_2$. The methanol formed is then distilled off slowly. The course of the reaction is followed by thin layer chromatography. The reaction is virtually complete after approx. 8 hours. The melt is dissolved in toluene while still warm and is purified with a customary adsorbent, such as "Tonsil". The toluene solution is evaporated and the residue is recrystallised. This gives 2-[2-hydroxy-3-tert.-butyl-5-(2-carbo-(2-ethylhexyl)-amidoethyl)-phenyl]-benztriazole. Melting point: 112°–113° C. (acetonitrile) (compound 72).

The procedure described in Example 9 is repeated, using the following amines instead of 2-ethylhexylamine: using dodecylamine, 2-[2-hydroxy-3-tert.-butyl-5-(2-carbododecylamidoethyl)-phenyl]-benztriazole is obtained. Melting point: 109°–111° C. (hexane) (compound 73).

Using cyclohexylamine, 2-[2-hydroxy-3-tert.-butyl-5-(2-carbocyclohexylamidoethyl)-phenyl]-benztriazole is obtained. Melting point: 172°–173° C. (toluene) (compound 74).

Using 3-(N-morpholinyl)-propylamine, 2-[2-hydroxy-3-tert.-butyl-5-(2-carbo-(3-(N-morpholinyl)-propyl)-amidoethyl)-phenyl]-benztriazole is obtained. Melting point: 104°–106° C. (acetonitrile) (compound 75).

Using 3-(octyloxy)-propylamine, 2-[2-hydroxy-3-tert.-butyl-5-(2-carbo-(3-(octyloxy)-propylamido)-ethyl)-phenyl]-benztriazole, melting point: 61°–63° C. (hexane) (compound 76) and 2-[2-hydroxy-3-tert.-butyl-5-(2-carbo-(3-(octyloxy)-propylamido)-ethyl)-phenyl]-5-chlorobenztriazole, melting point: 82°–83° C. (hexane) (compound 77) are obtained.

Using 3-hydroxypropylamine, 2-[2-hydroxy-3-tert.-butyl-5-(2-carbo-(3-hydroxypropyl)-amidoethyl)-phenyl]-benztriazole is obtained. Melting point: 132°–135° C. (acetonitrile) (compound 78).

Using tert.-octylamine (≡1,1,3,3-tetramethylbutylamine), 2-[2-hydroxy-3-tert.-butyl-5-(2-carbo-(1,1,3,3-tetramethyl)-butylamidoethyl)-phenyl]-benztriazole is obtained. Melting point: 157°–158° C. (ethyl acetate) (compound 79).

Using 5-hydroxy-3-oxapentylamine, 2-[2-hydroxy-3-tert.-butyl-5-(2-carbo-(5-hydroxy-3-oxa)-pentylamidoethyl)-phenyl]-benztriazole is obtained. Melting point: 115°–117° C. (acetonitrile) (compound 80).

Using 3-[4-(3-aminopropoxy)-butoxy]-propylamine,

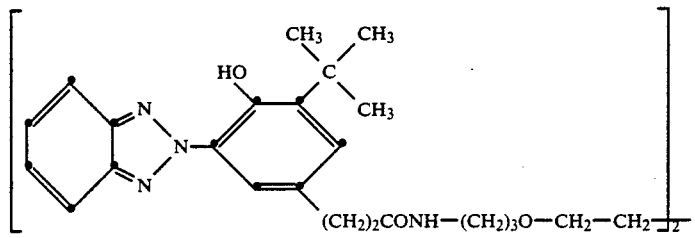

Using 4,7,10-trioxatetradecylamine, 2-[2-hydroxy-3-tert.-butyl-5-(2-carbo-(4,7,10-trioxatetradecyl)-amidoethyl)-phenyl]-benztriazole, melting point: 41°–43° C. (hexane) (compound 82), and 2-[2-hydroxy-3-tert.-butyl-5-(2-carbo-(4,7,10-trioxatetradecyl)-amidoethyl)-phenyl]-5-chlorobenztriazole, melting point: 59°–61° C. (hexane) (compound 83), are obtained.

Using hexamethylenediamine,

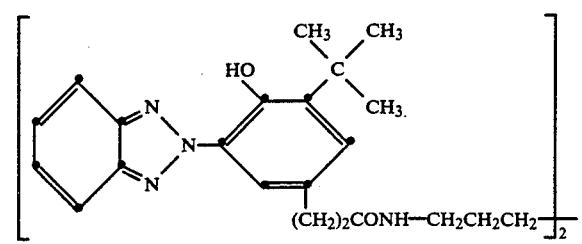

melting point: 211°–213° C. (toluene) (compound 84) is obtained.

By passing in ammonia, 2-[2-hydroxy-3-tert.-butyl-5-(2-carbamidoethyl)-phenyl]-benztriazole is obtained. Melting point: 159°–160° C. (acetonitrile) (compound 85).

EXAMPLE 10

33.9 g of 2-[2-hydroxy-3-tert.-butyl-5-(2-carboxyethyl)-phenyl]-benztriazole are suspended in 300 ml of toluene in a 1 l autoclave, 6.6 g (50% excess relative to molar equivalent) of ethylene oxide are added and the mixture is heated at an internal temperature of 80° C. for 12 hours. After cooling, the toluene solution is washed with dilute HCl solution and is washed again with dilute potassium carbonate solution. The organic phase is dried and evaporated and the residue is recrystallised. This gives 2-[2-hydroxy-3-tert.-butyl-5-(2-carbo-(2-hydroxyethyl)-phenyl]-benztriazole. Melting point: 101°–102° C. (toluene) (compound 86).

Using "chlorobenztriazolecarboxylic acid", 2-[2-hydroxy-3-tert.-butyl-5-(2-carbo-(2-hydroxyethyl)-phenyl]-5-chlorobenztriazole is obtained. Melting point: 120°–122° C. (ligroin) (compound 87).

If 0.1 mol of "benztriazolecarboxylic acid" and 0.05 mol of ethylene oxide are used and if the mixture is heated at an internal temperature of 150° C. for 10 hours, the following compounds are obtained:

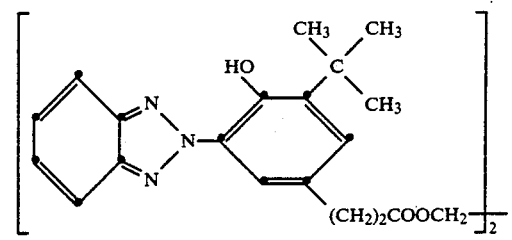

Melting point:
158–159° C.
(toluene)
(compound 81).

Melting point: 177–178° C.
(toluene) (compound 88)

-continued

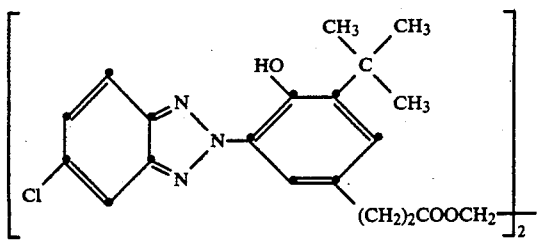

Melting point: 171-173° C.
(toluene) (compound 89).

EXAMPLE 11

10.8 g of 2-[2-hydroxy-3-tert.-butyl-5-(2-carbo-(2-hydroxyethoxy)-ethyl)-phenyl]-benztriazole (the compound from Example 10) in 100 ml of acetic anhydride are heated to approx. 80° C. The brownish-yellow solution is stirred for approx. 15 hours and is then cooled and discharged into water. The mixture is extracted with toluene and the toluene phase is washed again with dilute potassium carbonate solution and water. The toluene solution is then dried and evaporated. The residue is recrystallised from hexane. This gives 2-[2-hydroxy-3-tert.-butyl-5-(2-carbo-(2-acetoxyethoxy)-ethyl)-phenyl]-benztriazole. Melting point: 92°-93° C. (compound 90).

EXAMPLE 12

77.6 g of 2-[2-hydroxy-3-tert.-butyl-5-(2-carbomethoxyethyl)-phenyl]-5-chlorobenztriazole (compound 6) are initially taken in 300 ml of analytical grade toluene. 13.0 g of n-octanol and 15.7 g of 2-ethylhexanol are added and the solution is warmed to reflux temperature. 4.6 g of (±)-camphor-10-sulfonic acid (β) are added at 60° C. A methanol/toluene mixture is then distilled off slowly for approx. 8 hours, the amount distilled off being replaced by fresh toluene from time to time. A thin layer chromatogram indicates a virtually quantitative conversion after a reaction time of approx. 8 hours. The yellow solution is allowed to cool and is washed with approx. 1 liter of warm water, then with approx. 1 liter of 5% potassium carbonate solution and again with water. The organic layer is separated off and dried over anhydrous sodium sulfate. The toluene solution is then purified further with approx. 5 g of "Tonsil AC", filtered and evaporated. The residue is dried under a high vacuum of 0.04 mm Hg. This gives 89.7 g (92.3%) of a pale yellow oil, which is a mixture consisting of approx. 50% of 2-[2-hydroxy-3-tert.-butyl-5-(2-carbo-(2-ethylhexyloxy)-ethyl)-phenyl]-5-chlorobenztriazole (compound 22) and approx. 50% of 2-[2-hydroxy-3-tert.-butyl-5-(2-carbooctyloxyethyl)-phenyl]-5-chlorobenztriazole (compound 21).

The yellowish oil is analysed by NMR spectroscopy and gas chromatography.

| Elementary analysis gives the following figures: | |
|---|---|
| Calculated: C = 66.72% | Found: C = 66.84% |
| H = 7.46% | H = 7.73% |
| N = 8.64% | N = 8.60% |
| Cl = 7.29% | Cl = 7.45% |

Exactly the same procedure as described in the above example is repeated, using the unchlorinated benztriazolecarboxylic acid methyl ester (compound 5) instead of the chlorobenztriazole (compound 6). The product obtained is again a slightly yellowish oil, which is also a 1:1 mixture consisting of 2-[2-hydroxy-3-tert.-butyl-5-(2-carbooctyloxyethyl)-phenyl]-benztriazole (compound 8) and 2-[2-hydroxy-3-tert.-butyl-5-(2-carbo-(2-ethylhexyloxy)-ethyl)-phenyl]-benztriazole (compound 9).

| Elementary analysis: | |
|---|---|
| Calculated: C = 71.80% | Found: C = 72.17% |
| H = 8.25% | H = 8.31% |
| N = 9.31% | N = 9.23% |

Exactly the same procedure as described in Example 12 is repeated, using a mixture consisting of diethylene glycol monoethyl ether and diethylene glycol monobutyl ether instead of n-octanol and 2-ethylhexanol. Starting from the benztriazolecarboxylic acid methyl ester (compound 5), a slightly yellowish oil is again obtained, which is a 1:1 mixture consisting of 2-[2-hydroxy-3-tert.-butyl-5-(2-carbo-(3,6-dioxaoctyloxy)-ethyl)-phenyl]-benztriazole (compound 63) and 2-[2-hydroxy-3-tert.-butyl-5-(2-carbo-(3,6-dioxadecyloxy)-ethyl)-phenyl]-benztriazole (compound 65).

| Elementary analysis for the 1:1 mixture: | |
|---|---|
| Calculated: C = 66.50% | Found: C = 66.50% |
| H = 7.51% | H = 7.85% |
| N = 8.95% | N = 8.90% |

If the chlorobenztriazole acid methyl ester (compound 6) is used as the starting material, a yellowish oil is again obtained, which is a 1:1 mixture consisting of 2-[2-hydroxy-3-tert.-butyl-5-(2-carbo-(3,6-dioxaoctyloxy)-ethyl)-phenyl]-5-chlorobenztriazole (compound 64) and 2-[2-hydroxy-3-tert.-butyl-5-(2-carbo-(3,6-dioxadecyloxy)-ethyl)-phenyl]-5-chlorobenztriazole (compound 66).

| Elementary analysis for the 1:1 mixture: | |
|---|---|
| Calculated: | C = 61.96% | Found: | C = 62.21% |
| | H = 6.80% | | H = 6.70% |
| | N = 8.34% | | N = 8.36% |
| | Cl = 7.03% | | Cl = 7.05% |

USE EXAMPLES

EXAMPLE I:

The tendency of compounds 17, 18 and 21 to crystallise is tested in the following manner.

Solutions containing 0.5 mmol of each of these UV absorbers and varying amounts of tricresyl phosphate (TCP) and dibutyl phthalate (DBP) in 20 ml portions of methylene chloride are prepared, these solutions are warmed at 40° C. for approx. 5 hours in order to remove the bulk of the solvent and the samples are then kept in a high vacuum at 20° C. for 15 hours. The extent of crystallisation of the UV absorber in the samples is then assessed. The results are listed in Table 1.

TABLE 1

| | mg of product | 100 mg of TCP | 200 mg of TCP | 100 mg of DBP | 200 mg of DBP |
|---|---|---|---|---|---|
| Compound 21 | 241 | + | + | + | + |
| Compound 18 | 238 | + | + | + | + |

TABLE 1-continued

| | mg of product | 100 mg of TCP | 200 mg of TCP | 100 mg of DBP | 200 mg of DBP |
|---|---|---|---|---|---|
| Compound 17 | 224 | + | + | + | + |

+ = clear solution
— = crystallised

EXAMPLE II 3 photographic materials are prepared consisting of an opaque base coated with polyethylene, a light-sensitive layer (based on gelatine) applied to the base and containing silver bromide and a coupler, and a top layer (based on gelatine) containing in each case one of the following 3 UV absorbers according to the invention: compound 17, 18 or 21.

The following concentrations per unit area are obtained (the figures gives are for 1 m$^2$).

TABLE 2

| Component | AgBr layer | Top layer |
|---|---|---|
| Gelatine | 5.6 g | 7 g |
| Hardener A | — | 430 mg |
| Wetting agent (anionic) | 430 mg | 1,100 mg |
| Silver bromide | 520 mg | — |
| Tricresyl phosphate (TCP) | 1,060 mg | 0/2,500 mg |
| Magenta coupler | 207 mg | — |
| UV-absorber | — | 1.1 mmols |

The coupler and the hardener have the following structure:

Magenta coupler

[Structure of magenta coupler showing pyrazolone with NH linked to chlorophenyl, NHCOCH—O—phenyl—C(CH$_3$)(CH$_2$CH$_3$)(CH$_3$) side chain, and N-substituted 2,4,6-trichlorophenyl group, with (CH$_2$)$_{11}$CH$_3$ chain]

Hardener A

[Structure: dichlorotriazine linked via NH to phenyl-SO$_3^\ominus$Na$^\oplus$]

An image of a step wedge having a density difference of 0.15 logE per step is produced by exposure on each of the materials obtained and processing is then carried out in accordance with the instructions of the manufacturer, using the Kodak E+2 process for negative colour papers.

The diffuse reflectance density in the green is then measured for the magneta step at a density between 0.9 and 1.1 of the wedge. The wedge is then exposed in a daylight exposure apparatus at a total of 10,000 Langley units (41.9 KWs/cm$^2$) and the diffuse reflectance density is measured again.

The percentage losses in density listed in Table 5 can be calculated on the basis of the values thus obtained.

TABLE 3

| UV-absorber | Loss in density after 10,000 L | TCP |
|---|---|---|
| Blank sample | 84% | yes |
| Compound 21 | 42% | no |
| Compound 18 | 48% | yes |
| Compound 17 | 46% | yes |

It can be seen from this that the UV-absorbers according to the invention are at least equivalent to those of the state of the art in respect of protective action and in some cases even surpass them.

EXAMPLE III

Mixing the UV-absorbers according to the invention in masking transparent lacquers.

The following lacquers are taken as a basis:

(a) Base lacquer

| | | |
|---|---|---|
| Dynapol H 700 ®; Dynamit Nobel A.G. (polyester) | | 27.70 parts by weight |
| Mixture of | 21% of zirconyl diisooctoate | 1.2 parts by weight |
| | 4% of zirconyl monoisooctoate | |
| | 75% of mineral oil (boiling point 150–190° C.) | |
| CAB-EAB 531.1 ®, Eastman Kodak (cellulose acetobutyrate, 25% in 1:2 xylene/butyl acetate) | | 17.00 parts by weight |
| Maprenal MF 650 ®; Hoechst A.G. (melamine resin, 50% in butanol) | | 2.95 parts by weight |
| Solvesso 150 ®; Shell (solvent mixture) | | 10.55 parts by weight |
| Butyl acetate | | 21.10 parts by weight |
| Xylene | | 10.50 parts by weight |
| Sparkle Silver 5400 ® (Al pigment) | | 9.00 parts by weight |
| | | 100.00 parts by weight |

-continued (b) Transparent lacquer

| | |
|---|---|
| Viacryl VC 373 ®; Vianova A.G. (acrylic resin) | 58.30 parts by weight |
| Maprenal MF 590 ®; Hoechst A.G. | 27.30 parts by weight |
| Silicone oil, 1% in xylene | 1.00 parts by weight |
| Solvesso 150 ®; | 4.00 parts by weight |
| Xylene | 5.40 parts by weight |
| Ethylglycol acetate | 4.00 parts by weight |
| | 100.00 parts by weight |

The compounds according to the invention are previously dissolved in the spray thinner (1:1:1 xylene/butyl acetate/ethylglycol acetate) and are mixed into the transparent lacquer.

Metal sheets are lacquered by spray application. The film thicknesses are:

base lacquer: approx. 15μ
transparent lacquer: approx. 40μ

The criterion of effectiveness used is the stability to weathering of the top lacquer of the 2-layer metal effect coat of lacquer. The stabilising action manifests itself in longer weathering times before cracking occurs and before considerable loss in gloss, compared with the control sample.

The stabilising action is determined using the UV-CON ® rapid weathering apparatus (Atlas Electr. Dev. Comp., Chicago, Ill., U.S.A.); the cycle is: 4 hours of UV at 60° C.; 4 hours of condensation at 50° C. The following are determined: 20° gloss as specified in DIN 67,540; visual assessment of cracking.

The results of the tests are listed in Table 4.

TABLE 4

| Compound No. | 0.2% of the compound concerned | | 0.7% of the compound concerned | |
|---|---|---|---|---|
| | (hours) $t_{G/2}$ | (hours) $t_C$ | (hours) $t_{G/2}$ | (hours) $t_C$ |
| CONTROL | 800 | 2,600 | 800 | 2,600 |
| 16 | 1,800 | 3,800 | 1,500 | 3,400 |
| 20 | 1,500 | 3,600 | 1,400 | 2,600 |
| 19 | 1,500 | 3,600 | 1,200 | 2,600 |
| 17 | 1,500 | 3,400 | 1,700 | 2,600 |
| 15 | 1,500 | 3,600 | 2,700 | 3,600 |
| 51 | 1,900 | 3,600 | 1,700 | 3,400 |
| 33 | 1,100 | 3,400 | 1,300 | 3,200 |
| 67 | 1,000 | 2,600 | 1,500 | 3,400 |
| 72 | 900 | 2,600 | 2,200 | >3,800* |
| 73 | 1,700 | 3,600 | 1,900 | 3,600 |
| 65 | 1,200 | 2,600 | 1,400 | 2,600 |
| 76 | 1,400 | 2,600 | 1,300 | 2,600 |
| 80 | 1,400 | 2,600 | 2,300 | >3,800** |
| 67 | 1,100 | 2,600 | 1,900 | 3,600 |

*very dull after 3,800 hours
**very dull after 3,500 hours
$t_{G/2}$ time required for 50% loss of gloss
$t_C$ time required for cracking

EXAMPLE IV

Incorporation of the benztriazolecarboxylic acid in the synthesis of alkyd resins.

a) An alkyd resin is prepared in the manner which follows, based on a Shell (DX 49) recipe, in 2 stages using a 2 1 glass vessel equipped with a stirrer, an inert gas inlet and a reflux condenser fitted with a water separator.

The following amounts of starting substances are used:

Phthalic anhydride: 461.0 g
Dedico castor oil fatty acids: 175.5 g
Cardura E*: 381.5 g
Trimethylolethane: 182.0 g
Xylene: 60 ml

*Cardura E is a glycidyl ester of a monocarboxylic acid (see Shell leaflet for synthetic resins, dated 6.10.74).

The time sequence of the preparation is as follows:

| | Time | Temperature | Acid Number, mg of KOH/g | Water separation | |
|---|---|---|---|---|---|
| 1st stage | 0 | 23° C. | | | Cardura E and fatty acid charged; heating, stirrer and nitrogen switched on. |
| | 5 minutes | | | | Phthalic anhydride added. |
| | 30 minutes | 150° C. | | | Heating switched off at 140° C. Exothermic reaction. Heating if necessary in order to maintain the temperature of 150° C. |
| | 1 hour | 150° C. | | | WPE* 56,000. Heating switched off, cooling switched on. |
| 2nd stage | 15 minutes 1 hour 35 minutes | 120° C. | 120 | | Trimethylolethane, benztriazolecarboxylic acid in concentrations of 2 or 4 or 6% (relative to the total mixture) and xylene added. Heating switched on. |
| | 2 hours 40 minutes | 180° C. | | | |
| | 3 hours | 200° C. | | the first drops | |
| | 3 hours 30 minutes | 240° C. | | | Reaction temperature reached. |
| | 4 hours | 240° C. | 26.8 | 30 ml | |
| | 4 hours 30 minutes | 240° C. | 18.5 | 32 ml | |
| | 5 hours | 240° C. | 14.5 | 34 ml | |
| | 5 hours 15 minutes | | | | Heating switched off, mixture cooled and diluted. |

*WPE = epoxide equivalent weight

The reactants in the *first stage*, Cardura E, castor oil fatty acid and phthalic anhydride are charged into the kettle and the temperature is raised to 150° C. while passing nitrogen in slowly. The temperature is then kept at 150° C. until an epoxide equivalent weight of 50-70,000 has been reached (¾-1 hour). The batch is then cooled to about 120° C.

The batch is discontinued after reaching the following acid numbers.

| Benztriazolecarboxylic acid (% by weight) | Acid number (mg of KOH/g) |
|---|---|
| 2% | 14.5 |
| 4% | 16.5 |
| 6% | 16.8 |

After cooling, the alkyd resin solution is diluted with xylene and is applied to quartz plates in a dry film thickness of approx. 10μ.

The incorporation is checked by storing these samples for 10 days at a temperature of 100° C., and the losses of light stabiliser before and after storing under warm conditions are calculated from the UV transmission values.

TABLE 5

| Benztriazolecarboxylic acid (% by weight) | Losses after 10 days, storage under warm conditions (% by weight) |
|---|---|
| 2 | <5% |
| 4 | <5% |
| 6 | <5% |
| 4% (not co-condensed, for comparison) | 100% | b) An alkyd resin is prepared (Shell recipe DX 51) in a manner similar to that described under a).

1st stage:
Phthalic anhydride: 569.4 g
Glycerol: 23.4 g
Cardura E: 612.7 g
2nd stage:
Glycerol: 94.5 g
Xylene: 60 ml
The time sequence of the preparation is as follows:

The reactants of the first stage, Cardura E, phthalic anhydride and glycerol, are charged into the kettle and the temperature is raised to 150° C. while passing in nitrogen slowly. The temperature is maintained for ½ hour, then raised to 180° C. and kept at this level for about 15-30 minutes, until the measurement of epoxide equivalent weight indicates a value of 50,000 to 70,000, and the mixture is then cooled to 130°-140° C.

The quantity of glycerol for the second stage is then added, together with the benztriazolecarboxylic acid and xylene, and the temperature is raised to 190°-200° C. over a period of one hour. The temperature is increased to 230°-240° C., while maintaining continuous reflux, and is kept at this value until a final acid number of 13-17 mg of KOH/g is reached. The batch is then cooled and diluted with xylene to a solids content of 70%.

The following acid numbers are achieved:

| Benztriazolecarboxylic acid (% by weight) | Acid number (mg of KOH/g) |
|---|---|
| 2% | 17.1 |
| 4% | 13.0 |
| 6% | 13.8 |

The same procedure as described previously is followed to check the incorporation.

TABLE 6

| Benztriazolecarboxylic acid (% by weight) | Losses after 10 days, storage under warm conditions (% by weight) |
|---|---|
| 2 | <5% |
| 4 | <5% |
| 6 | <5% |

| | Time | Temperature | Acid Number, mg of KOH/g | Water separation | |
|---|---|---|---|---|---|
| 1st stage | 0 | 23° C. | | | The Cardura E, phthalic anhydride and the quantity of glycerol for the first stage are charged. The heating, the stirrer and the nitrogen are switched on. |
| | 40 minutes | 150° C. | | | Heating switched off. |
| | 1 hour 10 minutes | 150° C. | | | 130-140° C. Exothermic reaction. Heating maintained up to 180° C. |
| | 1 hour 20 minutes | 180° C. | | | |
| | 1 hour 30 minutes | 180° C. | | | Heating switched off, epoxide equivalent weight 66,000, cooling applied |
| 2nd stage | 1 hour 40 minutes | 140° C. | | | The quantity of glycerol for the second stage, benztriazolecarboxylic acid in concentrations of 2 or 4 or 6% and xylene are added. |
| | 2 hours 40 minutes | 200° C. | | the first drops | reflux |
| | 3 hours 30 minutes | 240° C. | | | |
| | 4 hours | 240° C. | 16.9 | 18 ml | |
| | 4 hours 30 minutes | 240° C. | 14.5 | 20 ml | |
| | 5 hours | 240° C. | 12.2 | 22 ml | |
| | 5 hours 15 minutes | 240° C. | | 24 ml | Heating switched off, product cooled and diluted. |

Solids content 70% by weight in xylene
Viscosity 48 P at 25° C.
Acid number 11.4 mg of KOH/g

EXAMPLE V a) In the test which follows, in addition to the magenta coupler (Example II), the following couplers are used:

Yellow coupler:

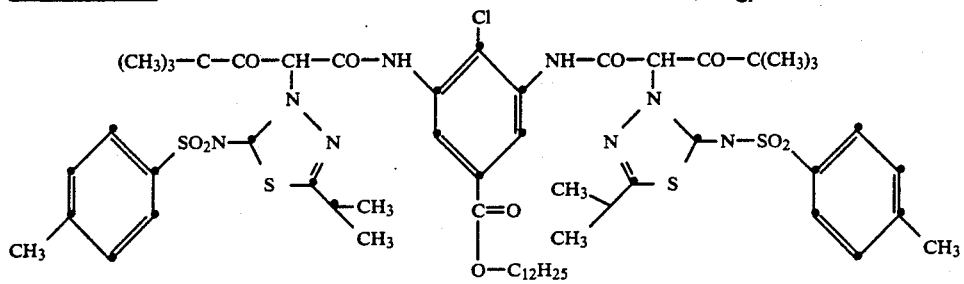

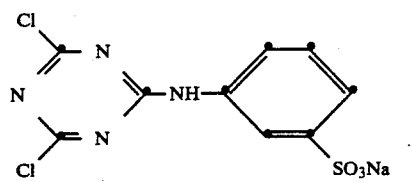

Cyan coupler:

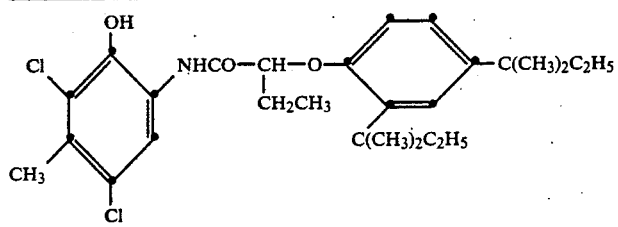

Various solutions are prepared by dissolving the amounts of coupler and UV-absorber indicated in Table 7 in 100 ml portions of ethyl acetate.

TABLE 7

| Solution No. | Coupler | Amount (mg) | Compound No. | Amount (mg) |
|---|---|---|---|---|
| 1 | Yellow coupler | 299 | L* | 226 + 226 |
| 2 | Yellow coupler | 299 | L | 151 + 151 |
| 3 | Yellow coupler | 299 | 62 | 499 |
| 4 | Yellow coupler | 299 | 62 | 333 |
| 5 | Yellow coupler | 299 | tricresyl phosphate | 300 |
| 6 | Magenta coupler | 194 | L | 226 + 226 |
| 7 | Magenta coupler | 194 | L | 151 + 151 |
| 8 | Magenta coupler | 194 | 62 | 499 |
| 9 | Magenta coupler | 194 | 62 | 333 |
| 10 | Magenta coupler | 194 | tricresyl phosphate | 300 |
| 11 | Cyan coupler | 124 | L | 226 + 226 |
| 12 | Cyan coupler | 124 | L | 151 + 151 |
| 13 | Cyan coupler | 124 | 62 | 499 |
| 14 | Cyan coupler | 124 | 62 | 333 |
| 15 | Cyan coupler | 124 | tricresyl phosphate | 300 |

*L is a 1:1 mixture of compounds 63 and 65.

Solutions 5, 10 and 15 contain tricresyl phosphate instead of the UV-absorber as a solvent for the coupler (blank sample).

2.0 ml of each of these solutions are added, in each case, to a mixture of 7.0 ml of a 6% gelatine solution (pH 6.5), 0.4 ml of an 8% solution in water of Triton 770 ® (an anionic wetting agent made by Rohm and Haas) and 0.6 ml of water, and the mixture is emulsified ultrasonically (5 minutes at 100 watts).

In each case, 2.8 ml of water, 0.7 ml of a 1% solution of the hardener of the formula and 2.0 ml of a silver bromide emulsion (7 g of silver per kg of emulsion) are added to 2.5 ml of each of the emulsions thus obtained. The mixture is then distributed uniformly on a plastic-coated sheet of paper measuring 13×18 cm, mounted on a glass plate.

After a drying time of 7 days at room temperature, images of 2 step wedges are produced by exposure in each case and processed by the Kodak Ektaprint+2 process, in accordance with the manufacturers' instructions. The samples thus obtained are then treated as follows: Fastness to light: irradiation in an Atlas Weather Ometer by means of a xenon lamp at the energy indicated in Table 8 and at 43° C. and 55% relative atmospheric humidity. Stability in the dark: the samples containing the cyan coupler are stored in the dark for 28 days at 60° C. and 70% relative atmospheric humidity.

Table 8 contains the losses in density as a percentage for an original density of 1.0 (diffuse reflectance).

TABLE 8

| | Fastness to light | | Stability in the dark |
|---|---|---|---|
| Sample No.* | Irradiation energy (kJ/cm²) | Loss in density (%) | Loss in density (%) |
| 1 | 21 | 23 | |
| 2 | 21 | 21 | |
| 3 | 21 | 25 | |
| 4 | 21 | 25 | |
| 5 (reference) | 21 | 40 | |
| 6 | 42 | 50 | |
| 7 | 42 | 56 | |
| 8 | 42 | 75 | |
| 9 | 42 | 77 | |
| 10 (reference) | 42 | 80 | |
| 11 | 63 | 21 | 13 |
| 12 | 63 | 24 | 17 |
| 13 | 63 | 22 | 8 |
| 14 | 63 | 25 | 6 |

TABLE 8-continued

| | Fastness to light | | Stability in the |
|---|---|---|---|
| Sample No.* | Irradiation energy (kJ/cm$^2$) | Loss in density (%) | dark Loss in density (%) |
| 15 (reference) | 63 | 27 | 25 |

*The sample No. is based in each case on the number of the solution in Table 7.

It can be seen from Table 8 that the compounds according to the present invention can also be employed as solvents for oil-soluble chromogenic couplers. When used in this way, there is a marked improvement in the fastness to light in the case of the yellow coupler and in the stability in the dark in the case of the cyan coupler.

b) In order to prevent the diffusion of oxidised developer substance into adjacent layers containing coupler and thus to improve the colour rendering, colour materials usually contain so-called interlayers which, in turn, often also contain a compound which is embedded so as to resist diffusion and which is capable of reacting with the oxidised developer to give colourless products, as a result of which the colour separation is improved even further.

The present example shows that the substances according to the invention are also suitable as solvents for such compounds.

A sample of material A of the following composition is prepared on a transparent base (the dispersions are prepared analogously to Example II):

1. Light-sensitive layer:

The layer contains, as the magenta coupler, the compound from Example II in a concentration per unit area of 450 mg/m$^2$, dissolved in tricresyl phosphate (concentration per unit area 180 mg/m$^2$), silver bromide in a concentration per unit area of 500 mg of silver per m$^2$, the hardener from Example II (concentration per unit area 69 mg/m$^2$) and gelatine. The layer thickness is 3.7 μm.

2. Interlayer:

The layer contains a dispersion of 2,5-di-tert.-octyl-hydroquinone (concentration per unit area 300 mg/m$^2$), dissolved in 600 mg of a 50:50 mixture of the compounds, according to the invention, Nos. 21 and 22, the hardener from Example II (concentration per unit area 48 mg/m$^2$) and gelatine. The layer thickenss is 3.0 μm.

3. Adjacent layer containing coupler:

The layer contains a dispersion of the cyan coupler from Example II (concentration per unit area 400 mg/m$^2$) in tricresyl phosphate (concentration per unit area 200 mg/m$^2$), the hardener from Example II (concentration per unit area 36 mg/m$^2$) and gelatine. The layer thickness is 2.2 μm.

4. Top layer:

The top layer contains gelatine and the hardener from Example II (concentration per unit area 35 mg/m$^2$). The layer thickness is 1.5 μm.

The following samples were also prepared:

Sample B: as sample A, but only gelatine in the interlayer

Sample C: as sample A, but the cyan coupler in the adjacent layer containing coupler is replaced by the yellow coupler from Example Va (concentration per unit area 500 mg/m$^2$)

Sample D: as sample C, but only gelatine in the interlayer.

The samples are subjected to total exposure and are processed as described under a).

The optical densities are then determined at 446 nm (absorption maximum of the yellow dye), 535 nm (absorption maximum of the magenta dye) and 662 nm (absorption maximum of the cyan dye). The corresponding values are shown in Table 9.

TABLE 9

| Sample | $D_{446\ nm}$ | $D_{535\ nm}$ | $D_{662\ nm}$ |
|---|---|---|---|
| A | 0.11 | 0.80 | 0.04 |
| B | 0.11 | 0.82 | 0.08 |
| C | 0.12 | 0.82 | 0.03 |
| D | 0.16 | 0.83 | 0.03 |

It can be seen clearly from the data in Table 9 that, as a result of embedding a mixture of 2,5-di-tert.-octylhydroquinone and the compounds, according to the invention, Nos. 21 and 22, the formation of cyan or yellow dyestuff, respectively, in an adjacent layer is suppressed markedly.

The samples are then irradiated in an Atlas Weather Ometer at a total energy of 21 kJ/cm$^2$. The losses in density at 535 nm are shown below:

TABLE 10

| Samples | Percentage loss in density |
|---|---|
| A | 26 |
| B | 53 |
| C | 28 |
| D | 53 | c) The example shows that the compounds of the present invention can also be used as solvents for other UV-absorbers, whereby it is possible to obtain a desired spectral absorption, depending on the absorption spectra.

Solutions of compounds No. 63 and No. 65 of the present invention and 2-[2-hydroxy-3-(1-methyl-propyl)-5-tert.-butyl-phenyl]-2H-benztriazole (compound Q) in ethyl acetate are dispersed in an aqueous gelatine solution as described in Example II. The hardener of Example II (7 mmols/100 g of gelatine) is added to the emulsions thus obtained and the mixtures are distributed on subbed glass plates, the concentrations per unit area listed in Table 11 being obtained.

The concentration of gelatine per unit area is 4.8 g/m$^2$ in all cases.

TABLE 11

| | Concentrations per unit area mg/m$^2$ | | | | | | | |
|---|---|---|---|---|---|---|---|---|
| Sample | Compound 63 | Compound 65 | Compound Q | $D_{max}$ | $\lambda_{max}$ | $D_{380\ nm}{}^{(1)}$ | $D_{390\ nm}{}^{(1)}$ | $D_{400\ nm}{}^{(1)}$ |
| E | 300 | 300 | 123 | 2.15 | 350 | 1.02 | 0.47 | 0.14 |
| F | 225 | 225 | 246 | 2.30 | 349 | 1.03 | 0.46 | 0.14 |
| G | 150 | 150 | 370 | 2.41 | 348 | 0.98 | 0.41 | 0.14 |

TABLE 11-continued

| Sample | Concentrations per unit area mg/m² | | | $D_{max}$ | $\lambda_{max}$ | $D_{380 nm}$[1] | $D_{390 nm}$[1] | $D_{400 nm}$[1] |
|---|---|---|---|---|---|---|---|---|
| | Compound 63 | Compound 65 | Compound Q | | | | | |
| H | 75 | 75 | 490 | 2.54 | 346 | 0.84 | 0.28 | 0.08 |

[1]Optical density at the corresponding wavelength d) The dye of the formula

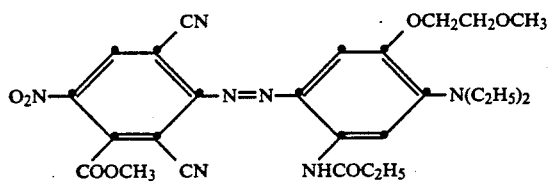

is dissolved, on the one hand, in a 1:1 mixture of the compounds, according to the invention, No. 21 and No. 22 and, on the other hand, in tricresyl phosphate, using ethyl acetate as an auxiliary solvent, and is dispersed as described in Example II. After adding a silver bromide emulsion, the dispersion is coated onto plastic-coated paper as described in Example Va, the following concentrations per unit area being obtained:

| Component | Sample I | Sample K (comparison sample) |
|---|---|---|
| Dye | 118 mg/m² | 118 mg/m² |
| Compound No. 21 | 1.07 g/m² | — |
| Compound No. 22 | 1.07 g/m² | — |
| Tricresyl phosphate | — | 2.4 g/m² |
| Silver | 507 mg/m² | 507 mg/m² |
| Gelatine | 8.3 g/m² | 8.3 g/m² |
| Hardener (see under a) | 490 mg/m² | 490 mg/m² |

The light-sensitive material thus obtained is exposed behind a step wedge and is processed as follows at 24° C.:

Developing: 6 minutes
Washing: 4 minutes
Silver bleaching and dye bleaching: 6 minutes
Washing: 2 minutes
Fixing: 8 minutes
Washing: 6 minutes
Drying The developing and fixing baths are customary baths such as are used in black and white photography. The silver dye bleach bath has the following composition per liter of solution:

Sulfamic acid: 100 g
m-Nitrobenzenesulfonic acid: 10 g
Potassium iodide: 6 g
2,3,6-Trimethylquinoxaline: 2 g
4-Mercaptobutyric acid: 1 g After determining the colour density, the colour wedges thus obtained are irradiated at a total energy of 21 kJ/cm² in an Atlas Weather Ometer, equipped with a xenon lamp, and the colour density is then determined again. Starting from a density of 1.0, the following decreases in density are found:

Sample I: 0.31
Sample K (comparison sample): 0.44

It can be seen from this that the light-fastness of dyes for the silver dye bleach process can be increased by using the compounds according to the invention as solvents for the dyes concerned.

We claim:
1. A stabilized organic material containing an effective stabilizing amount of at least one compound of the formula I

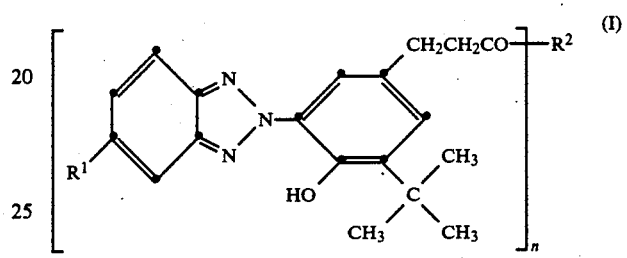

in which $R^1$ is H, Cl, straight-chain or branched $C_1$–$C_4$ alkyl or straight-chain or branched $C_1$–$C_4$ alkoxy and n is one of the numbers 1 or 2, and in which, a) when n=1, $R^2$ is Cl, —$OR^3$ or

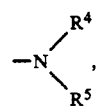

and
b) when n=2, $R^2$ is one of the divalent radicals —O—$R^9$—O— or

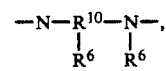

$R^3$ being H, straight-chain or branched $C_1$–$C_{18}$ alkyl which is unsubstituted or substituted by 1 to 3 OH groups or

or —O—Si($R^6$)$_3$ or —O—CO($R^6$), straight-chain or branched $C_3$–$C_{18}$ alkyl which is interrupted by —O—, —S— or —$NR^6$— and which can be unsubstituted or substituted by OH or —O—CO($R^6$), $C_5$–$C_{12}$ cycloalkyl which is unsubstituted or substituted by OH, straight-chain or branched $C_2$–$C_{18}$ alkenyl which is unsubstituted or substituted by OH, $C_7$–$C_{15}$ aralkyl,

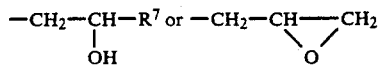

and $R^4$ and $R^5$ independently of one another being H, straight-chain or branched $C_1$–$C_{18}$ alkyl, straight-chain or branched C$_3$–C$_{18}$ alkyl which is interrupted by O, S or —NR$^6$—, C$_5$–C$_{12}$ cycloalkyl, C$_6$–C$_{14}$ aryl which is substituted or unsubstituted, straight-chain or branched C$_3$–C$_8$ alkenyl, C$_7$–C$_{15}$ aralkyl, C$_6$–C$_{14}$ aryl or C$_1$–C$_3$ hydroxyalkyl, or R$_4$ and R$_5$, together with the nitrogen atom, are a pyrrolidine, piperidine, piperazine or morpholine ring, and R$_6$ being H, straight-chain or branched C$_1$–C$_{18}$ alkyl, C$_5$–C$_{12}$ cycloalkyl, straight-chain or branched C$_3$–C$_8$ alkenyl, C$_6$–C$_{14}$ aryl or C$_7$–C$_{18}$ aralkyl, R$_7$ being H, straight-chain or branched C$_1$–C$_{18}$ alkyl which is unsubstituted or substituted by —PO(OR$^8$)$_2$, phenyl which is unsubstituted or substituted by OH, C$_7$–C$_{18}$ aralkyl or —CH$_2$OR$^8$, R$^8$ being straight-chain or branched C$_1$–C$_{18}$ alkyl, straight-chain or branched C$_3$–C$_{18}$ alkenyl, C$_5$–C$_{10}$ cycloalkyl, C$_6$–C$_{16}$ aryl or C$_7$–C$_{15}$ aralkyl, R$_9$ being C$_2$–C$_8$ alkylene, C$_4$–C$_8$ alkenylene, C$_4$ alkinylene, cyclohexylene, straight-chain or branched C$_4$–C$_{10}$ alkylene which is interrupted by —O—, or

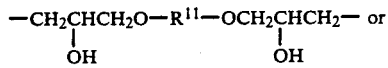

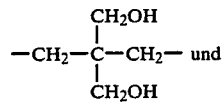

and R$_{10}$ being straight-chain or branched C$_2$–C$_{12}$ alkylene which may be interrupted by —O—, cyclohexylene,

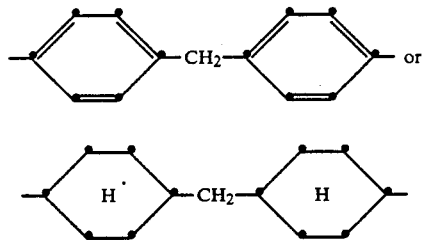

or R$^{10}$ and R$^6$, together with the two nitrogen atoms, being a piperazine ring, and R$^{11}$ being straight-chain or branched C$_2$–C$_8$ alkylene, straight-chain or branched C$_4$–C$_{10}$ alkylene which is interrupted by —O—, cycloalkylene, arylene,

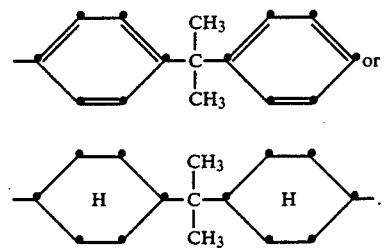

2. The material of claim 1 wherein R$^1$ is H or Cl, n is the number 1 and R$^2$ is —OR$^3$ or

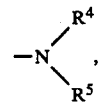

R$^3$ being straight-chain or branched C$_4$–C$_{12}$alkyl, straight-chain or branched C$_3$–C$_{10}$alkyl which is interrupted by O, cyclohexyl or

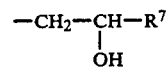

which is uninterrupted by O, cyclohexyl or

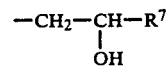

which is unsubstituted or substituted by OH, R$^4$ and R$^5$ independently of one another being straight-chain or branched C$_4$–C$_{12}$ alkyl, straight-chain or branched C$_3$–C$_{10}$ alkyl which is interrupted by O, or cyclohexyl, R$^7$ being straight-chain or branched C$_1$–C$_{12}$ alkyl which is unsubstituted or substituted by

or —CH$_2$OR$^8$, and R$^8$ being straight-chain or branched C$_1$–C$_{12}$ alkyl or cyclohexyl.

3. The material of claim 1 wherein R$^1$ is H or Cl, n is the number 2 and R$^2$ is one of the divalent radicals —O—R$^9$—O— or

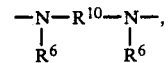

R$^6$ being H or C$_1$–C$_8$alkyl, R$^9$ being C$_2$–C$_6$alkylene, straight-chain or branched C$_4$–C$_{10}$alkylene which is interrupted by —O—, or

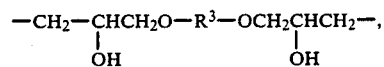

R$^{10}$ being straight-chain or branched C$_2$–C$_{12}$alkylene and R$^{11}$ being C$_2$–C$_6$alkylene or straight-chain or branched C$_4$–C$_{10}$alkylene which is interrupted by —O—.

4. The material of claim 1 wherein the compound of formula I is 2-[2-hydroxy-3-tert.butyl-5-(2-carbo-n-octyloxyethyl)-phenyl]-benztriazole or 2-{2-hydroxy-3-tert.-butyl-5-[2-carbo-(2-ethylhexyl)-oxyethyl]-phenyl}-benztriazole or 2-[2-hydroxy-3-tert.-butyl-5-(2-carbo-n-octyloxyethyl)-phenyl]-5-chlorobenztriazole or 2-{2-hydroxy-3-tert.-butyl-5-[2-carbo-(2-ethylhexyl)-oxyethyl]-phenyl}-5-chlorobenztriazole or of the formula

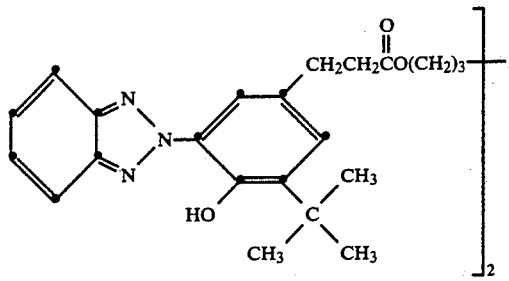

5. The material of claim 1, wherein the compound of formula I is a mixture of 2-[2-hydroxy-3-tert.-butyl-5-(2-carbo-n-octyloxyethyl)-phenyl]-5-chlorobenztriazole and 2-{2-hydroxy-3-tert.-butyl-5-[2-carbo-(2-ethylhexyl)-oxyethyl]-phenyl}-5-chlorobenztriazole in a ratio by weight of 1:1.

6. The material of claim 1, which contains 0.1 to 5% by weight of said compound.

7. The material of claim 1, which is a synthetic polymer.

8. The material of claim 7, which is a polyester, polycarbonate, acrylic resin which can be crosslinked by heat, thermoplastic acrylic resin, polyamide, MF resin, UF resin or a polyurethane.

9. A stabilized lacquer based on one or more of the polymers according to claim 8.

10. The material of claim 1 which is in the form of photographic material or part of a photographic material, the photographic material containing 0.1 to 5% by weight of a compound of the formula I.

* * * * *